US008763878B2

(12) United States Patent
Euteneuer et al.

(10) Patent No.: US 8,763,878 B2
(45) Date of Patent: Jul. 1, 2014

(54) METHODS AND APPARATUS HAVING BOWSTRING-LIKE STAPLE DELIVERY TO A TARGET TISSUE

(75) Inventors: Charles L. Euteneuer, St. Michael, MN (US); Rebecca McCarville, Spring Park, MN (US); Duane Frion, Brooklyn Center, MN (US); Nathaniel Zenz-Olson, Blaine, MN (US); Diane M. Feehan, Corcoran, MN (US)

(73) Assignee: Rotation Medical, Inc., Plymouth, MN (US)

( * ) Notice: Subject to any disclaimer, the term of this patent is extended or adjusted under 35 U.S.C. 154(b) by 316 days.

(21) Appl. No.: 12/794,677

(22) Filed: Jun. 4, 2010

(65) Prior Publication Data

US 2011/0000950 A1 Jan. 6, 2011

Related U.S. Application Data

(60) Provisional application No. 61/184,198, filed on Jun. 4, 2009, provisional application No. 61/253,800, filed on Oct. 21, 2009, provisional application No. 61/313,051, filed on Mar. 11, 2010.

(51) Int. Cl.
*A61B 17/10* (2006.01)
*A61B 17/04* (2006.01)

(52) U.S. Cl.
USPC ..................................... 227/179.1; 227/177.1

(58) Field of Classification Search
USPC ........................................... 227/175.1–182.1
See application file for complete search history.

(56) References Cited

U.S. PATENT DOCUMENTS

| 511,238 A | 12/1893 | Hieatzman et al. |
| 765,793 A | 7/1904 | Ruckel |
| 1,728,316 A | 9/1929 | von Wachenfeldt et al. |
| 1,855,546 A | 4/1932 | File |

(Continued)

FOREIGN PATENT DOCUMENTS

| CA | 2390508 A1 | 5/2001 |
| EP | 0142225 A1 | 5/1985 |

(Continued)

OTHER PUBLICATIONS

Euteneuer, Charles L.; U.S. Appl. No. 13/397,573 entitled "Methods and Apparatus for Fixing Sheet-Like Materials to a Target Tissue," filed Feb. 15, 2012.

(Continued)

*Primary Examiner* — Robert Long
(74) *Attorney, Agent, or Firm* — Seager, Tufte & Wickhem LLC

(57) ABSTRACT

Devices for attaching a sheet-like implant to a target tissue include a sheath and a staple push rod. The sheath has a distal end configured to be pressed against the target tissue. The staple push rod is disposed within at least a portion of the sheath and is slidable relative thereto. The staple push rod includes a pair of stakes. Each stake is dimensioned to abut a surface of a staple to apply pushing forces thereto. The stakes are biased to assume a bow-like shape such that an intermediate portion of a staple extends tautly between the first stake and the second stake when the stakes are extending beyond the distal end of the tubular member. Methods for attaching a sheet-like implant to a target tissue are also disclosed.

20 Claims, 22 Drawing Sheets

(56) References Cited

U.S. PATENT DOCUMENTS

| | | |
|---|---|---|
| 1,868,100 A | 7/1932 | Goodstein |
| 1,910,688 A | 5/1933 | Goodstein |
| 1,940,351 A | 12/1933 | Howard |
| 2,034,785 A | 3/1936 | Wappler |
| 2,075,508 A | 3/1937 | Davidson |
| 2,131,321 A | 9/1938 | Hart |
| 2,158,242 A | 5/1939 | Maynard |
| 2,199,025 A | 4/1940 | Conn |
| 2,201,610 A | 5/1940 | Dawson, Jr. |
| 2,254,620 A | 9/1941 | Miller |
| 2,277,931 A | 3/1942 | Moe |
| 2,283,814 A | 5/1942 | La Place |
| 2,316,297 A | 4/1943 | Southerland et al. |
| 2,421,193 A | 5/1947 | Gardner |
| 2,571,813 A | 10/1951 | Austin |
| 2,630,316 A | 3/1953 | Foster |
| 2,684,070 A | 7/1954 | Kelsey |
| 2,744,251 A | 5/1956 | Vollmer |
| 2,790,341 A | 4/1957 | Keep et al. |
| 2,817,339 A | 12/1957 | Sullivan |
| 2,825,162 A | 3/1958 | Flood |
| 2,881,762 A | 4/1959 | Lowrie |
| 2,910,067 A | 10/1959 | White |
| 3,068,870 A | 12/1962 | Levin |
| 3,077,812 A | 2/1963 | Dietrich |
| 3,103,666 A | 9/1963 | Bone |
| 3,123,077 A | 3/1964 | Alcamo |
| 3,209,754 A | 10/1965 | Brown |
| 3,221,746 A | 12/1965 | Noble |
| 3,470,834 A | 10/1969 | Bone |
| 3,527,223 A | 9/1970 | Shein |
| 3,570,497 A | 3/1971 | Lemole |
| 3,577,837 A | 5/1971 | Bader, Jr. |
| 3,579,831 A | 5/1971 | Stevens et al. |
| 3,643,851 A | 2/1972 | Green et al. |
| 3,687,138 A | 8/1972 | Jarvik |
| 3,716,058 A | 2/1973 | Tanner, Jr. |
| 3,717,294 A | 2/1973 | Green |
| 3,757,629 A | 9/1973 | Schneider |
| 3,777,538 A | 12/1973 | Weatherly et al. |
| 3,837,555 A * | 9/1974 | Green .................. 227/130 |
| 3,845,772 A | 11/1974 | Smith |
| 3,875,648 A | 4/1975 | Bone |
| 3,960,147 A | 6/1976 | Murray |
| 3,976,079 A | 8/1976 | Samuels et al. |
| 4,014,492 A | 3/1977 | Rothfuss |
| 4,127,227 A | 11/1978 | Green |
| 4,259,959 A | 4/1981 | Walker |
| 4,263,903 A | 4/1981 | Griggs |
| 4,265,226 A | 5/1981 | Cassimally |
| 4,317,451 A | 3/1982 | Cerwin et al. |
| 4,400,833 A | 8/1983 | Kurland |
| 4,422,567 A | 12/1983 | Haynes |
| 4,454,875 A | 6/1984 | Pratt et al. |
| 4,480,641 A | 11/1984 | Failla et al. |
| 4,485,816 A | 12/1984 | Krumme |
| 4,526,174 A | 7/1985 | Froehlich |
| 4,549,545 A | 10/1985 | Levy |
| 4,570,623 A * | 2/1986 | Ellison et al. .................. 606/75 |
| 4,595,007 A | 6/1986 | Mericle |
| 4,624,254 A | 11/1986 | McGarry et al. |
| 4,627,437 A * | 12/1986 | Bedi et al. .................. 606/220 |
| 4,632,100 A | 12/1986 | Somers et al. |
| 4,635,637 A | 1/1987 | Schreiber |
| 4,669,473 A | 6/1987 | Richards et al. |
| 4,696,300 A | 9/1987 | Anderson |
| 4,719,917 A | 1/1988 | Barrows et al. |
| 4,738,255 A | 4/1988 | Goble et al. |
| 4,741,330 A | 5/1988 | Hayhurst |
| 4,762,260 A | 8/1988 | Richards et al. |
| 4,799,495 A | 1/1989 | Hawkins et al. |
| 4,809,695 A | 3/1989 | Gwathmey et al. |
| 4,851,005 A | 7/1989 | Hunt et al. |
| 4,858,608 A | 8/1989 | McQuilkin |
| 4,884,572 A | 12/1989 | Bays et al. |
| 4,887,601 A | 12/1989 | Richards |
| 4,924,866 A | 5/1990 | Yoon |
| 4,930,674 A * | 6/1990 | Barak .................. 227/179.1 |
| 4,968,315 A | 11/1990 | Gatturna |
| 4,976,715 A | 12/1990 | Bays et al. |
| 4,994,073 A | 2/1991 | Green |
| 4,997,436 A | 3/1991 | Oberlander |
| 5,002,563 A | 3/1991 | Pyka et al. |
| 5,013,316 A | 5/1991 | Goble et al. |
| 5,015,249 A | 5/1991 | Nakao et al. |
| 5,037,422 A | 8/1991 | Hayhurst et al. |
| 5,041,129 A | 8/1991 | Hayhurst et al. |
| 5,046,513 A | 9/1991 | Gatturna et al. |
| 5,053,047 A | 10/1991 | Yoon |
| 5,059,206 A * | 10/1991 | Winters .................. 606/213 |
| 5,062,563 A | 11/1991 | Green et al. |
| 5,100,417 A | 3/1992 | Cerier et al. |
| 5,102,421 A | 4/1992 | Anspach, Jr. |
| 5,116,357 A | 5/1992 | Eberbach |
| 5,122,155 A | 6/1992 | Eberbach |
| 5,123,913 A | 6/1992 | Wilk et al. |
| RE34,021 E | 8/1992 | Mueller et al. |
| 5,141,515 A | 8/1992 | Eberbach |
| 5,141,520 A | 8/1992 | Goble et al. |
| 5,156,609 A | 10/1992 | Nakao et al. |
| 5,156,616 A | 10/1992 | Meadows et al. |
| 5,167,665 A | 12/1992 | McKinney |
| 5,171,259 A | 12/1992 | Inoue |
| 5,174,295 A | 12/1992 | Christian et al. |
| 5,174,487 A | 12/1992 | Rothfuss et al. |
| 5,176,682 A | 1/1993 | Chow |
| 5,176,692 A | 1/1993 | Wilk et al. |
| 5,203,787 A | 4/1993 | Noblitt et al. |
| 5,217,472 A | 6/1993 | Green et al. |
| 5,224,946 A | 7/1993 | Hayhurst et al. |
| 5,242,457 A | 9/1993 | Akopov et al. |
| 5,246,441 A | 9/1993 | Ross et al. |
| 5,251,642 A | 10/1993 | Handlos |
| 5,261,914 A | 11/1993 | Warren |
| 5,269,753 A | 12/1993 | Wilk |
| 5,269,783 A | 12/1993 | Sander |
| 5,282,829 A | 2/1994 | Hermes |
| 5,289,963 A | 3/1994 | McGarry et al. |
| 5,290,217 A | 3/1994 | Campos |
| 5,290,296 A * | 3/1994 | Phillips .................. 606/144 |
| 5,304,187 A | 4/1994 | Green et al. |
| 5,333,624 A | 8/1994 | Tovey |
| 5,342,396 A | 8/1994 | Cook |
| 5,350,400 A | 9/1994 | Esposito et al. |
| 5,352,229 A * | 10/1994 | Goble et al. .................. 606/75 |
| 5,354,292 A | 10/1994 | Braeuer et al. |
| 5,364,408 A | 11/1994 | Gordon |
| 5,366,460 A | 11/1994 | Eberbach |
| 5,370,650 A * | 12/1994 | Tovey et al. .................. 606/151 |
| 5,372,604 A | 12/1994 | Trott |
| 5,380,334 A | 1/1995 | Torrie et al. |
| 5,383,477 A | 1/1995 | Dematteis |
| 5,397,332 A | 3/1995 | Kammerer et al. |
| 5,403,326 A * | 4/1995 | Harrison et al. .................. 606/139 |
| 5,405,360 A | 4/1995 | Tovey |
| 5,411,522 A | 5/1995 | Trott |
| 5,411,523 A | 5/1995 | Goble |
| 5,417,691 A | 5/1995 | Hayhurst |
| 5,417,712 A | 5/1995 | Whittaker et al. |
| 5,425,490 A * | 6/1995 | Goble et al. .................. 227/175.1 |
| 5,441,502 A | 8/1995 | Bartlett |
| 5,441,508 A | 8/1995 | Gazielly et al. |
| 5,456,720 A | 10/1995 | Schultz et al. |
| 5,464,403 A | 11/1995 | Kieturakis et al. |
| 5,478,354 A | 12/1995 | Tovey et al. |
| 5,486,197 A | 1/1996 | Le et al. |
| 5,497,933 A * | 3/1996 | DeFonzo et al. .................. 227/175.1 |
| 5,500,000 A | 3/1996 | Feagin et al. |
| 5,501,695 A | 3/1996 | Anspach, Jr. et al. |
| 5,503,623 A | 4/1996 | Tilton, Jr. |
| 5,505,735 A | 4/1996 | Li |
| 5,507,754 A | 4/1996 | Green et al. |
| 5,520,700 A | 5/1996 | Beyar et al. |
| 5,522,817 A | 6/1996 | Sander et al. |

(56) References Cited

U.S. PATENT DOCUMENTS

| | | | |
|---|---|---|---|
| 5,545,180 A | 8/1996 | Le et al. |
| 5,560,532 A | 10/1996 | Defonzo et al. |
| 5,562,689 A | 10/1996 | Green et al. |
| 5,569,306 A | 10/1996 | Thal |
| 5,582,616 A | 12/1996 | Bolduc et al. |
| 5,584,835 A | 12/1996 | Greenfield |
| 5,618,314 A | 4/1997 | Harwin et al. |
| 5,622,257 A | 4/1997 | Deschenes et al. |
| 5,628,751 A | 5/1997 | Sander et al. |
| 5,643,319 A | 7/1997 | Green et al. |
| 5,643,321 A | 7/1997 | McDevitt |
| 5,647,874 A | 7/1997 | Hayhurst |
| 5,649,963 A | 7/1997 | McDevitt |
| 5,662,683 A | 9/1997 | Kay |
| 5,667,513 A | 9/1997 | Torrie et al. |
| 5,674,245 A | 10/1997 | Ilgen |
| 5,681,342 A | 10/1997 | Benchetrit |
| 5,702,215 A | 12/1997 | Li |
| 5,713,903 A | 2/1998 | Sander et al. |
| 5,720,753 A | 2/1998 | Sander et al. |
| 5,725,541 A | 3/1998 | Anspach, III et al. |
| 5,741,282 A | 4/1998 | Anspach, III et al. |
| 5,766,246 A | 6/1998 | Mulhauser et al. |
| 5,782,864 A | 7/1998 | Lizardi |
| 5,797,909 A | 8/1998 | Michelson |
| 5,797,931 A | 8/1998 | Bito et al. |
| 5,797,963 A | 8/1998 | McDevitt |
| 5,807,403 A | 9/1998 | Beyar et al. |
| 5,830,221 A | 11/1998 | Stein et al. |
| 5,836,961 A | 11/1998 | Kieturakis et al. |
| 5,868,762 A | 2/1999 | Cragg et al. |
| 5,873,891 A | 2/1999 | Sohn |
| 5,885,294 A | 3/1999 | Pedlick et al. |
| 5,893,856 A | 4/1999 | Jacob et al. |
| 5,904,696 A | 5/1999 | Rosenman |
| 5,919,184 A | 7/1999 | Tilton, Jr. |
| 5,922,026 A | 7/1999 | Chin |
| 5,928,244 A | 7/1999 | Tovey et al. |
| 5,948,000 A | 9/1999 | Larsen et al. |
| 5,957,939 A | 9/1999 | Heaven et al. |
| 5,957,953 A | 9/1999 | Dipoto et al. |
| 5,968,044 A | 10/1999 | Nicholson et al. |
| 5,980,557 A | 11/1999 | Iserin et al. |
| 5,989,265 A | 11/1999 | Bouquet De La Joliniere et al. |
| 5,997,552 A | 12/1999 | Person et al. |
| 6,063,088 A | 5/2000 | Winslow |
| 6,156,045 A | 12/2000 | Ulbrich et al. |
| 6,179,840 B1 | 1/2001 | Bowman |
| 6,193,731 B1 | 2/2001 | Oppelt et al. |
| 6,193,733 B1 | 2/2001 | Adams |
| 6,245,072 B1 | 6/2001 | Zdeblick et al. |
| 6,302,885 B1 | 10/2001 | Essiger |
| 6,312,442 B1 | 11/2001 | Kieturakis et al. |
| 6,315,789 B1 | 11/2001 | Cragg |
| 6,318,616 B1 * | 11/2001 | Pasqualucci et al. ............ 227/83 |
| 6,322,563 B1 | 11/2001 | Cummings et al. |
| 6,325,805 B1 | 12/2001 | Ogilvie et al. |
| 6,387,113 B1 | 5/2002 | Hawkins et al. |
| 6,391,333 B1 | 5/2002 | Li et al. |
| 6,413,274 B1 | 7/2002 | Pedros |
| 6,425,900 B1 | 7/2002 | Knodel et al. |
| 6,436,110 B2 | 8/2002 | Bowman et al. |
| 6,447,522 B2 | 9/2002 | Gambale et al. |
| 6,447,524 B1 | 9/2002 | Knodel et al. |
| 6,478,803 B1 | 11/2002 | Kapec et al. |
| 6,482,178 B1 | 11/2002 | Andrews et al. |
| 6,482,210 B1 | 11/2002 | Skiba et al. |
| 6,506,190 B1 | 1/2003 | Walshe |
| 6,511,499 B2 | 1/2003 | Schmieding et al. |
| 6,517,564 B1 | 2/2003 | Grafton et al. |
| 6,524,316 B1 | 2/2003 | Nicholson et al. |
| 6,527,795 B1 | 3/2003 | Lizardi |
| 6,530,933 B1 | 3/2003 | Yeung et al. |
| 6,540,769 B1 | 4/2003 | Miller, III |
| 6,551,333 B2 | 4/2003 | Kuhns et al. |
| 6,554,852 B1 | 4/2003 | Oberlander |
| 6,569,186 B1 | 5/2003 | Winters et al. |
| 6,575,976 B2 | 6/2003 | Grafton |
| 6,599,289 B1 | 7/2003 | Bojarski et al. |
| 6,620,185 B1 | 9/2003 | Harvie et al. |
| 6,629,988 B2 | 10/2003 | Weadock |
| 6,638,297 B1 | 10/2003 | Huitema |
| 6,648,893 B2 | 11/2003 | Dudasik |
| 6,666,872 B2 | 12/2003 | Barreiro et al. |
| 6,673,094 B1 | 1/2004 | McDevitt et al. |
| 6,685,728 B2 | 2/2004 | Sinnott et al. |
| 6,692,506 B1 | 2/2004 | Ory et al. |
| 6,723,099 B1 | 4/2004 | Goshert |
| 6,726,704 B1 | 4/2004 | Loshakove et al. |
| 6,726,705 B2 | 4/2004 | Peterson et al. |
| 6,740,100 B2 | 5/2004 | Demopulos et al. |
| 6,746,472 B2 | 6/2004 | Frazier et al. |
| 6,764,500 B1 | 7/2004 | Van De Moer et al. |
| 6,770,073 B2 | 8/2004 | McDevitt et al. |
| 6,779,701 B2 | 8/2004 | Bailly et al. |
| 6,800,081 B2 | 10/2004 | Parodi |
| 6,835,206 B2 * | 12/2004 | Jackson ..................... 623/17.11 |
| 6,849,078 B2 | 2/2005 | Durgin et al. |
| 6,887,259 B2 | 5/2005 | Lizardi |
| 6,926,723 B1 | 8/2005 | Mulhauser et al. |
| 6,932,834 B2 | 8/2005 | Lizardi et al. |
| 6,939,365 B1 | 9/2005 | Fogarty et al. |
| 6,946,003 B1 | 9/2005 | Wolowacz et al. |
| 6,949,117 B2 | 9/2005 | Gambale et al. |
| 6,964,685 B2 | 11/2005 | Murray et al. |
| 6,966,916 B2 | 11/2005 | Kumar |
| 6,972,027 B2 | 12/2005 | Fallin et al. |
| 6,984,241 B2 | 1/2006 | Lubbers et al. |
| 6,991,597 B2 | 1/2006 | Gellman et al. |
| 7,008,435 B2 * | 3/2006 | Cummins ..................... 606/139 |
| 7,021,316 B2 | 4/2006 | Leiboff |
| 7,025,772 B2 | 4/2006 | Gellman et al. |
| 7,033,379 B2 | 4/2006 | Peterson |
| 7,037,324 B2 | 5/2006 | Martinek |
| 7,048,171 B2 * | 5/2006 | Thornton et al. .......... 227/176.1 |
| 7,063,711 B1 | 6/2006 | Loshakove et al. |
| 7,083,638 B2 | 8/2006 | Foerster |
| 7,087,064 B1 | 8/2006 | Hyde |
| 7,112,214 B2 | 9/2006 | Peterson et al. |
| 7,118,581 B2 | 10/2006 | Fridén |
| 7,144,413 B2 | 12/2006 | Wilford et al. |
| 7,144,414 B2 | 12/2006 | Harvie et al. |
| 7,150,750 B2 | 12/2006 | Damarati |
| 7,153,314 B2 | 12/2006 | Laufer et al. |
| 7,160,314 B2 | 1/2007 | Sgro et al. |
| 7,160,326 B2 | 1/2007 | Ball |
| 7,163,551 B2 * | 1/2007 | Anthony et al. .............. 606/219 |
| 7,163,563 B2 | 1/2007 | Schwartz et al. |
| 7,169,157 B2 | 1/2007 | Kayan |
| 7,189,251 B2 | 3/2007 | Kay |
| 7,201,754 B2 | 4/2007 | Stewart et al. |
| 7,214,232 B2 | 5/2007 | Bowman et al. |
| 7,226,469 B2 | 6/2007 | Benavitz et al. |
| 7,229,452 B2 | 6/2007 | Kayan |
| 7,247,164 B1 | 7/2007 | Ritchart et al. |
| 7,303,577 B1 | 12/2007 | Dean |
| 7,309,337 B2 | 12/2007 | Colleran et al. |
| 7,320,692 B1 * | 1/2008 | Bender et al. ................. 606/139 |
| 7,320,701 B2 | 1/2008 | Haut et al. |
| 7,322,935 B2 | 1/2008 | Palmer et al. |
| 7,326,231 B2 | 2/2008 | Phillips et al. |
| 7,343,920 B2 | 3/2008 | Toby et al. |
| 7,368,124 B2 | 5/2008 | Chun et al. |
| 7,377,934 B2 | 5/2008 | Lin et al. |
| 7,381,213 B2 | 6/2008 | Lizardi |
| 7,390,329 B2 | 6/2008 | Westra et al. |
| 7,399,304 B2 | 7/2008 | Gambale et al. |
| 7,404,824 B1 | 7/2008 | Webler et al. |
| 7,416,554 B2 | 8/2008 | Lam et al. |
| 7,452,368 B2 | 11/2008 | Liberatore et al. |
| 7,460,913 B2 | 12/2008 | Kuzma et al. |
| 7,463,933 B2 | 12/2008 | Wahlstrom et al. |
| 7,465,308 B2 | 12/2008 | Sikora et al. |
| 7,481,832 B1 * | 1/2009 | Meridew et al. .............. 606/319 |

(56) References Cited

U.S. PATENT DOCUMENTS

| | | | |
|---|---|---|---|
| 7,485,124 B2 | 2/2009 | Kuhns et al. | |
| 7,497,854 B2 | 3/2009 | Gill et al. | |
| 7,500,972 B2 | 3/2009 | Voegele et al. | |
| 7,500,980 B2 | 3/2009 | Gill et al. | |
| 7,500,983 B1 | 3/2009 | Kaiser et al. | |
| 7,503,474 B2 | 3/2009 | Hillstead et al. | |
| 7,506,791 B2 | 3/2009 | Omaits et al. | |
| 7,559,941 B2 | 7/2009 | Zannis et al. | |
| 7,572,276 B2 | 8/2009 | Lim et al. | |
| 7,585,311 B2 | 9/2009 | Green et al. | |
| 7,766,208 B2* | 8/2010 | Epperly et al. | 227/175.1 |
| 7,771,440 B2* | 8/2010 | Ortiz et al. | 606/142 |
| 7,776,057 B2* | 8/2010 | Laufer et al. | 606/139 |
| 7,780,685 B2* | 8/2010 | Hunt et al. | 606/151 |
| 7,785,255 B2* | 8/2010 | Malkani | 600/235 |
| 7,807,192 B2 | 10/2010 | Li et al. | |
| 7,819,880 B2 | 10/2010 | Zannis et al. | |
| 7,918,879 B2 | 4/2011 | Yeung et al. | |
| 8,114,101 B2* | 2/2012 | Criscuolo et al. | 606/151 |
| 8,197,837 B2 | 6/2012 | Jamiolkowski et al. | |
| 2002/0077687 A1 | 6/2002 | Ahn | |
| 2002/0090725 A1 | 7/2002 | Simpson et al. | |
| 2002/0117534 A1* | 8/2002 | Green et al. | 227/176.1 |
| 2002/0123767 A1 | 9/2002 | Prestel | |
| 2002/0165559 A1* | 11/2002 | Grant et al. | 606/139 |
| 2003/0073979 A1 | 4/2003 | Naimark et al. | |
| 2003/0125748 A1 | 7/2003 | Li et al. | |
| 2003/0212456 A1 | 11/2003 | Lipchitz et al. | |
| 2004/0059416 A1 | 3/2004 | Murray et al. | |
| 2004/0138705 A1 | 7/2004 | Heino et al. | |
| 2004/0167519 A1 | 8/2004 | Weiner et al. | |
| 2005/0015021 A1 | 1/2005 | Shiber | |
| 2005/0049618 A1 | 3/2005 | Masuda et al. | |
| 2005/0051597 A1* | 3/2005 | Toledano | 227/176.1 |
| 2005/0059996 A1* | 3/2005 | Bauman et al. | 606/215 |
| 2005/0060033 A1 | 3/2005 | Vacanti et al. | |
| 2005/0107807 A1 | 5/2005 | Nakao | |
| 2005/0113736 A1 | 5/2005 | Orr et al. | |
| 2005/0171569 A1 | 8/2005 | Girard et al. | |
| 2005/0187576 A1* | 8/2005 | Whitman et al. | 606/219 |
| 2005/0240222 A1* | 10/2005 | Shipp | 606/219 |
| 2005/0274768 A1* | 12/2005 | Cummins et al. | 227/175.1 |
| 2006/0074423 A1 | 4/2006 | Alleyne et al. | |
| 2006/0178743 A1 | 8/2006 | Carter | |
| 2006/0235442 A1 | 10/2006 | Huitema | |
| 2006/0293760 A1 | 12/2006 | Dedeyne | |
| 2007/0078477 A1 | 4/2007 | Heneveld, Sr. et al. | |
| 2007/0083236 A1 | 4/2007 | Sikora et al. | |
| 2007/0112361 A1 | 5/2007 | Schonholz et al. | |
| 2007/0179531 A1 | 8/2007 | Thornes | |
| 2007/0185506 A1 | 8/2007 | Jackson | |
| 2007/0190108 A1 | 8/2007 | Datta et al. | |
| 2007/0219558 A1 | 9/2007 | Deutsch | |
| 2007/0270804 A1 | 11/2007 | Chudik | |
| 2007/0288023 A1 | 12/2007 | Pellegrino et al. | |
| 2008/0027470 A1 | 1/2008 | Hart et al. | |
| 2008/0051888 A1 | 2/2008 | Ratcliffe et al. | |
| 2008/0065153 A1 | 3/2008 | Allard et al. | |
| 2008/0090936 A1 | 4/2008 | Fujimura et al. | |
| 2008/0125869 A1* | 5/2008 | Paz et al. | 623/23.72 |
| 2008/0135600 A1* | 6/2008 | Hiranuma et al. | 227/176.1 |
| 2008/0173691 A1* | 7/2008 | Mas et al. | 227/175.1 |
| 2008/0188874 A1 | 8/2008 | Henderson | |
| 2008/0188936 A1 | 8/2008 | Ball et al. | |
| 2008/0195119 A1 | 8/2008 | Ferree | |
| 2008/0200949 A1* | 8/2008 | Hiles et al. | 606/215 |
| 2008/0241213 A1 | 10/2008 | Chun et al. | |
| 2008/0272173 A1* | 11/2008 | Coleman et al. | 227/175.1 |
| 2008/0306408 A1 | 12/2008 | Lo | |
| 2009/0001122 A1* | 1/2009 | Prommersberger et al. | 227/176.1 |
| 2009/0012521 A1 | 1/2009 | Axelson, Jr. et al. | |
| 2009/0030434 A1* | 1/2009 | Paz et al. | 606/151 |
| 2009/0069806 A1* | 3/2009 | De La Mora Levy et al. | 606/46 |
| 2009/0076541 A1 | 3/2009 | Chin et al. | |
| 2009/0105535 A1* | 4/2009 | Green et al. | 600/106 |
| 2009/0112085 A1 | 4/2009 | Eby | |
| 2009/0134198 A1* | 5/2009 | Knodel et al. | 227/176.1 |
| 2009/0156986 A1 | 6/2009 | Trenhaile | |
| 2009/0156997 A1 | 6/2009 | Trenhaile | |
| 2009/0182245 A1 | 7/2009 | Zambelli | |
| 2009/0242609 A1* | 10/2009 | Kanner | 227/175.1 |
| 2009/0314820 A1* | 12/2009 | Green et al. | 227/176.1 |
| 2010/0145367 A1 | 6/2010 | Ratcliffe | |
| 2010/0147922 A1* | 6/2010 | Olson | 227/176.1 |
| 2010/0163598 A1* | 7/2010 | Belzer | 227/181.1 |
| 2010/0241227 A1 | 9/2010 | Euteneuer et al. | |
| 2010/0249801 A1 | 9/2010 | Sengun et al. | |
| 2010/0256675 A1 | 10/2010 | Romans | |
| 2010/0274278 A1 | 10/2010 | Fleenor et al. | |
| 2010/0292715 A1* | 11/2010 | Nering et al. | 606/151 |
| 2010/0292791 A1 | 11/2010 | Lu et al. | |
| 2010/0327042 A1* | 12/2010 | Amid et al. | 227/176.1 |
| 2011/0011917 A1* | 1/2011 | Loulmet | 227/181.1 |
| 2011/0034942 A1 | 2/2011 | Levin et al. | |
| 2011/0040310 A1 | 2/2011 | Levin et al. | |
| 2011/0040311 A1 | 2/2011 | Levin et al. | |
| 2011/0066166 A1 | 3/2011 | Levin et al. | |
| 2011/0106154 A1 | 5/2011 | DiMatteo et al. | |
| 2011/0114700 A1* | 5/2011 | Baxter et al. | 227/179.1 |
| 2011/0224702 A1 | 9/2011 | Van Kampen et al. | |
| 2011/0264149 A1 | 10/2011 | Pappalardo et al. | |
| 2012/0100200 A1* | 4/2012 | Belcheva et al. | 424/423 |
| 2012/0160893 A1* | 6/2012 | Harris et al. | 227/175.1 |
| 2012/0193391 A1* | 8/2012 | Michler et al. | 227/175.1 |
| 2012/0211543 A1* | 8/2012 | Euteneuer | 227/175.1 |
| 2012/0248171 A1* | 10/2012 | Bailly et al. | 227/176.1 |
| 2013/0153627 A1 | 6/2013 | Euteneuer et al. | |
| 2013/0153628 A1 | 6/2013 | Euteneuer | |
| 2013/0158554 A1 | 6/2013 | Euteneuer et al. | |
| 2013/0158587 A1 | 6/2013 | Euteneuer et al. | |
| 2013/0158661 A1 | 6/2013 | Euteneuer et al. | |
| 2013/0172920 A1 | 7/2013 | Euteneuer et al. | |
| 2013/0172997 A1 | 7/2013 | Euteneuer et al. | |
| 2013/0184716 A1 | 7/2013 | Euteneuer et al. | |

FOREIGN PATENT DOCUMENTS

| | | |
|---|---|---|
| EP | 0298400 A1 | 1/1989 |
| EP | 0390613 A1 | 10/1990 |
| EP | 0543499 A1 | 5/1993 |
| EP | 0548998 A1 | 6/1993 |
| EP | 0557963 A1 | 9/1993 |
| EP | 0589306 A2 | 3/1994 |
| EP | 0908152 A1 | 4/1999 |
| EP | 1491157 A1 | 12/2004 |
| EP | 1559379 A1 | 8/2005 |
| EP | 2030576 A2 | 3/2009 |
| GB | 2154688 A | 9/1985 |
| GB | 2397240 A | 7/2004 |
| JP | 58-188442 | 11/1983 |
| JP | 2005506122 | 3/2005 |
| JP | 2006515774 | 6/2006 |
| WO | WO 85/05025 | 11/1985 |
| WO | WO 01/76456 A2 | 10/2001 |
| WO | WO 02/34140 A2 | 5/2002 |
| WO | WO 03/105670 A2 | 12/2003 |
| WO | WO 2004/000138 A1 | 12/2003 |
| WO | WO 2004/093690 A1 | 11/2004 |
| WO | WO 2005/016389 A2 | 2/2005 |
| WO | WO 2006/086679 A1 | 8/2006 |
| WO | WO 2007/014910 A2 | 2/2007 |
| WO | WO 2007/030676 A2 | 3/2007 |
| WO | WO 2007/078978 A2 | 7/2007 |
| WO | WO 2007/082088 A2 | 7/2007 |
| WO | WO 2008/111073 A2 | 9/2008 |
| WO | WO 2008/111078 A2 | 9/2008 |
| WO | WO 2008/139473 A2 | 11/2008 |
| WO | WO 2009/079211 A1 | 6/2009 |

(56) References Cited

FOREIGN PATENT DOCUMENTS

| WO | WO 2009143331 A1 | * | 11/2009 | ........... A61B 17/072 |
|---|---|---|---|---|
| WO | WO 2011/095890 A2 | | 8/2011 | |
| WO | WO 2011/128903 A2 | | 10/2011 | |

OTHER PUBLICATIONS

Euteneuer et al.; U.S. Appl. No. 13/397,603 entitled "Methods and Apparatus for Delivering and Positioning Sheet-Like Materials," filed Feb. 15, 2012.

Alexander et al.; Ligament and tendon repair with an absorbable polymer-coated carbon fiber stent; Bulletin of the Hospital for Joint Diseases Orthopaedic Institute; vol. 46; No. 2; pp. 155-173; 1986.

Bahler et al.; Trabecular bypass stents decrease intraocular pressure in cultured himan anterior segments; Am. J. Opthalmology; vol. 138; No. 6; pp. 988-994; Dec. 2004.

Chamay et al.; Digital contracture deformity after implantation of a silicone prosthesis: Light and electron microscopic study; The Journal of Hand Surgery; vol. 3; No. 3; pp. 266-270; May 1978.

D'Ermo et al.; Our results with the operation of ab externo; Ophthalmologica; vol. 168; pp. 347-355; 1971.

France et al.; Biomechanical evaluation of rotator cuff fixation methods; The American Journal of Sports Medicine; vol. 17; No. 2; 1989.

Goodship et al.; An assessment of filamentous carbon fibre for the treatment of tendon injury in the horse; Veterinary Record; vol. 106; pp. 217-221; Mar. 8, 1980.

Hunter et al.; Flexor-tendon reconstruction in severely damaged hands; The Journal of Bone and Joint Surgery (American Volume); vol. 53-A; No. 5; pp. 329-358; Jul. 1971.

Johnstone et al.; Microsurgery of Schlemm's canal and the human aqueous outflow system; Am. J. Opthalmology; vol. 76; No. 6; pp. 906-917; Dec. 1973.

Kowalsky et al.; Evaluation of suture abrasion against rotator cuff tendon and proximal humerus bone; Arthroscopy: The Journal of Arthroscopic and Related Surgery; vol. 24; No. 3; pp. 329-334; Mar. 2008.

Lee et al.; Aqueous-venous and intraocular pressure. Preliminary report of animal studies; Investigative Ophthalmology; vol. 5; No. 1; pp. 59-64; Feb. 1966.

Maepea et al.; The pressures in the episcleral veins, Schlemm's canal and the trabecular meshwork in monkeys: Effects of changes in intraocular pressure; Exp. Eye Res.; vol. 49; pp. 645-663; 1989.

Nicolle et al.; A silastic tendon prosthesis as an adjunct to flexor tendon grafting: An experimental and clinical evaluation; British Journal of Plastic Surgery; vol. 22; Issues 3-4; pp. 224-236; 1969.

Rubin et al.; The use of acellular biologic tissue patches in foot and ankle surgery; Clinics in Podiatric Medicine and Surgery; nol. 22; pp. 533-552; 2005.

Schultz; Canaloplasty procedure shows promise for open-angle glaucoma in European study; Ocular Surgery News; pp. 34-35; Mar. 1, 2007.

Spiegel et al.; Schlemm's canal implant: A new method to lower intraocular pressure in patients with POAG; Ophthalmic Surgery and Lasers; vol. 30; No. 6; pp. 492-494; Jun. 1999.

Valdez et al.; Repair of digital flexor tendon lacerations in the horse, using carbon fiber implants; JAYMA; vol. 177; No. 5; pp. 427-435; Sep. 1, 1980.

Euteneuer et al.; U.S. Appl. No. 12/684,774 entitled "Implantable Tendon Protection Systems and Related Kits and Methods," filed Jan. 8, 2010.

Euteneuer et al.; U.S. Appl. No. 12/794,540 entitled "Methods and Apparatus for Fixing Sheet-Like Materials to a Target Tissue," filed Jun. 4, 2010.

Euteneuer et al.; U.S. Appl. No. 12/794,551 entitled "Methods and Apparatus for Delivering Staples to a Target Tissue," filed Jun. 4, 2010.

Euteneuer et al.; U.S. Appl. No. 12/794,673 entitled "Methods and Apparatus for Deploying Sheet-Like Materials," filed Jun. 4, 2010.

Stetson et al.; Arthroscopic treatment of partial rotator cuff tears; Operative Techniques in Sports Medicine; vol. 12, Issue 2; pp. 135-148; Apr. 2004.

Wikipedia, the free encyclopedia; Rotator cuff tear; downloaded from <http://en.wikipedia.org/wiki/Rotator_cuff_tear> on Dec. 6, 2012; 14 pages.

Euteneuer et al.; U.S. Appl. No. 13/889,675 entitled "Methods and Apparatus for Fixing Sheet-Like Materials to a Target Tissue," filed May 8, 2013.

Euteneuer et al.; U.S. Appl. No. 13/889,687 entitled "Methods and Apparatus for Delivering Staples to a Target Tissue," filed May 8, 2013.

Van Kampen et al.; U.S. Appl. No. 13/889,701 entitled "Tendon repair implant and method of arthroscopic implantation," filed May 8, 2013.

Euteneuer et al.; U.S. Appl. No. 13/889,722 entitled "Apparatus and Method for Forming Pilot Holes in Bone and Delivering Fasteners Therein for Retaining an Implant," filed May 8, 2013.

Euteneuer et al.; U.S. Appl. No. 13/889,737 entitled "Fasteners and Fastener Delivery Devices for Affixing Sheet-Like Materials to Bone or Tissue," filed May 8, 2013.

Euteneuer et al.; U.S. Appl. No. 13/889,757 entitled "Methods and Apparatus for Delivering and Positioning Sheet-Like Materials in Surgery," filed May 8, 2013.

Euteneuer et al.; U.S. Appl. No. 13/889,774 entitled "Guidewire Having a Distal Fixation Member for Delivering and Positioning Sheet-Like Materials in Surgery," filed May 8, 2013.

Euteneuer et al.; U.S. Appl. No. 13/889,832 entitled "Anatomical location Markers and Methods of Use in Positioning Sheet-Like Materials During Surgery," filed May 8, 2013.

* cited by examiner

METHODS AND APPARATUS HAVING BOWSTRING-LIKE STAPLE DELIVERY TO A TARGET TISSUE

CROSS REFERENCE TO RELATED APPLICATIONS

The present application claims the benefit of U.S. Provisional Patent Application Ser. No. 61/184,198 filed on Jun. 4, 2009; U.S. Provisional Patent Application Ser. No. 61/253,800 filed on Oct. 21, 2009; and U.S. Provisional Patent Application No. 61/313,051 file on Mar. 11, 2010, the disclosures of each incorporated herein by reference.

INCORPORATION BY REFERENCE

The present application is related to U.S. patent application Ser. No. 12/794,540, entitled Methods and Apparatus for Fixing Sheet-like Materials to a Target Tissue, filed on Jun. 4, 2010; U.S. patent application Ser. No. 12/794,551,entitled Methods and Apparatus for Delivering Staples to a Target Tissue, filed on Jun. 4, 2010; and, U.S. patent application Ser. No. 12/794,673, entitled Methods and Apparatus for Deploying Sheet-like Materials, filed on Jun. 4, 2010, the disclosures of each incorporated herein by reference.

All publications and patent applications mentioned in this specification are herein incorporated by reference to the same extent as if each individual publication or patent application was specifically and individually indicated to be incorporated by reference.

FIELD OF THE INVENTION

The present invention relates generally to orthopedic medicine and surgery. More particularly, the present invention relates to methods and apparatus for delivery and fixation of sheet-like materials, such as for treating articulating joints.

BACKGROUND OF THE INVENTION

The glenohumeral joint of the shoulder is found where the head of the humerus mates with a shallow depression in the scapula. This shallow depression is known as the the glenoid fossa. Six muscles extend between the humerus and scapula and actuate the glenohumeral joint. These six muscles include the deltoid, the teres major, and the four rotator cuff muscles. As disclosed by Ball et al. in U.S. Patent Publication No. US 2008/0188936 A1 and as illustrated in FIG. 1 the rotator cuff muscles are a complex of four muscles. These four muscles are the supraspinatus, the infraspinatus, the subscapularis, and the teres minor. The centering and stabilizing roles played by the rotator cuff muscles are critical to the proper function of the shoulder. The rotator cuff muscles provide a wide variety of moments to rotate the humerus and to oppose unwanted components of the deltoid and pectoralis muscle forces.

The four muscles of the rotator cuff arise from the scapula 12. The distal tendons of the rotator cuff muscles splay out and interdigitate to form a common continuous insertion on the humerus 14. The subscapularis 16 arises from the anterior aspect of the scapula 12 and attaches over much of the lesser tuberosity of the humerous. The supraspinatus muscle 18 arises from the supraspinatus fossa of the posterior scapula, passes beneath the acromion and the acromioclavicular joint, and attaches to the superior aspect of the greater tuberosity 11. The infraspinatus muscle 13 arises from the infraspinous fossa of the posterior scapula and attaches to the posterolateral aspect of the greater tuberosity 11. The teres minor 15 arises from the lower lateral aspect of the scapula 12 and attaches to the lower aspect of the greater tuberosity 11.

The mechanics of the rotator cuff muscles 10 are complex. The rotator cuff muscles 10 rotate the humerus 14 with respect to the scapula 12, compress the humeral head 17 into the glenoid fossa providing a critical stabilizing mechanism to the shoulder (known as concavity compression), and provide muscular balance. The supraspinatus and infraspinatus provide 45 percent of abduction and 90 percent of external rotation strength. The supraspinatus and deltoid muscles are equally responsible for producing torque about the shoulder joint in the functional planes of motion.

The rotator cuff muscles 10 are critical elements of this shoulder muscle balance equation. The human shoulder has no fixed axis. In a specified position, activation of a muscle creates a unique set of rotational moments. For example, the anterior deltoid can exert moments in forward elevation, internal rotation, and cross-body movement. If forward elevation is to occur without rotation, the cross-body and internal rotation moments of this muscle must be neutralized by other muscles, such as the posterior deltoid and infraspinatus. The timing and magnitude of these balancing muscle effects must be precisely coordinated to avoid unwanted directions of humeral motion. Thus the simplified view of muscles as isolated motors, or as members of force couples must give way to an understanding that all shoulder muscles function together in a precisely coordinated way—opposing muscles canceling out undesired elements leaving only the net torque necessary to produce the desired action. Injury to any of these soft tissues can greatly inhibit ranges and types of motion of the arm.

With its complexity, range of motion and extensive use, a fairly common soft tissue injury is damage to the rotator cuff or rotator cuff tendons. Damage to the rotator cuff is a potentially serious medical condition that may occur during hyperextension, from an acute traumatic tear or from overuse of the joint. With its critical role in abduction, rotational strength and torque production, the most common injury associated with the rotator cuff region is a strain or tear involving the supraspinatus tendon. A tear in the supraspinitus tendon 19 is schematically depicted in FIG. 2. A tear at the insertion site of the tendon with the humerus, may result in the detachment of the tendon from the bone. This detachment may be partial or full, depending upon the severity of the injury. Additionally, the strain or tear can occur within the tendon itself. Injuries to the supraspinatus tendon 19 and recognized modalities for treatment are defined by the type and degree of tear. The first type of tear is a full thickness tear as also depicted in FIG. 2, which as the term indicates is a tear that extends through the thickness of the supraspinatus tendon regardless of whether it is completely torn laterally. The second type of tear is a partial thickness tear which is further classified based on how much of the thickness is torn, whether it is greater or less than 50% of the thickness.

The accepted treatment for a full thickness tear or a partial thickness tear greater than 50% includes reconnecting the torn tendon via sutures. For the partial thickness tears greater than 50%, the tear is completed to a full thickness tear by cutting the tendon prior to reconnection. In contrast to the treatment of a full thickness tear or a partial thickness tear of greater than 50%, the treatment for a partial thickness tear less than 50% usually involves physical cessation from use of the tendon, i.e., rest. Specific exercises can also be prescribed to strengthen and loosen the shoulder area. In many instances, the shoulder does not heal and the partial thickness tear can be the source of chronic pain and stiffness. Further, the pain and stiffness may cause restricted use of the limb which tends to result in further degeneration or atrophy in the shoulder. Surgical intervention may be required for a partial thickness tear of less than 50%, however, current treatment interventions do not include repair of the tendon, rather the surgical procedure is directed to arthroscopic removal of bone to relieve points of impingement or create a larger tunnel between the tendon and bone that is believed to be causing tendon damage. As part of the treatment, degenerated tendon may also be removed using a debridement procedure in which tendon material is ablated. Again, the tendon partial tear is not repaired. Several authors have reported satisfactory early post operative results from these procedures, but over time recurrent symptoms have been noted. In the event of recurrent symptoms, many times a patient will "live with the pain". This may result in less use of the aim and shoulder which further causes degeneration of the tendon and may lead to more extensive damage. A tendon repair would then need to be done in a later procedure if the prescribed treatment for partial tear was unsuccessful in relieving pain and stiffness or over time the tear propagated through injury or degeneration to a full thickness tear or a partial thickness tear greater than 50% with attendant pain and debilitation. A subsequent later procedure would include the more drastic procedure of completing the tear to full thickness and suturing the ends of the tendon back together. This procedure requires extensive rehabilitation, has relatively high failure rates and subjects the patient who first presented and was treated with a partial thickness tear less than 50% to a second surgical procedure.

As described above, adequate treatments do not currently exist for repairing a partial thickness tear of less than 50% in the supraspinatus tendon. Current procedures attempt to alleviate impingement or make room for movement of the tendon to prevent further damage and relieve discomfort but do not repair or strengthen the tendon. Use of the still damaged tendon can lead to further damage or injury. Prior damage may result in degeneration that requires a second more drastic procedure to repair the tendon. Further, if the prior procedure was only partially successful in relieving pain and discomfort, a response may be to use the shoulder less which leads to degeneration and increased likelihood of further injury along with the need for more drastic surgery. There is a large need for surgical techniques and systems to treat partial thickness tears of less than 50% and prevent future tendon damage by strengthening or repairing the native tendon having the partial thickness tear.

SUMMARY OF THE INVENTION

According to aspects of the invention, devices for attaching a sheet-like implant to a target tissue are disclosed. In some embodiments, the device includes a sheath and a staple push rod. The sheath has a distal end configured to be pressed against the target tissue. The staple push rod is disposed within at least a portion of the sheath and is slidable relative thereto. The staple push rod includes a pair of stakes. Each stake is dimensioned to abut a surface of a staple to apply pushing forces thereto. The stakes are biased to assume a bow-like shape such that an intermediate portion of a staple extends tautly between the first stake and the second stake when the stakes are extending beyond the distal end of the tubular member.

In some embodiments, each stake has a distal portion and a proximal portion. Each distal portion is dimensioned to extend into a passage defined by a staple. Each proximal portion has a width larger than a width of each distal portion so that a shoulder of each proximal portion contacts a proximal surface of the staple to apply pushing forces thereto. In some embodiments, the stakes are biased to expand against an inner surface of the sheath. The intermediate portion of the staple may include a first arm, a second arm, and a bridge. The first stake and the second stake may extend away from each other when the stakes are assuming the bow-like shape.

In some embodiments, the device further comprising a sheath having a proximal end, a distal end and a lumen extending therebetween. In these embodiments, at least a portion of the staple push rod extends into the lumen and is slidable relative thereto. The first stake and the second stake may be disposed in the lumen of the sheath. In some embodiments, the sheath defines a distal opening fluidly communicating with the lumen. The staple push rod is slidably disposed in the lumen so as to urge relative movement between the stakes and the sheath. With this arrangement, the stakes can be advanced through the distal opening defined by the sheath so that the stakes are free to assume the bow-like shape.

In some embodiments, the stakes have a first lateral extent when the stakes are free to assume the bow-like shape. The lumen of the sheath has a lumen dimension smaller than the first lateral extent. In some embodiments, the sheath holds the stakes in a compact configuration. In some embodiments, the stakes are sufficiently flexible to allow the stakes to be advanced into the lumen of the sheath. A distal-most portion of each stake may extend across a leading edge of each fluke of a staple.

According to aspects of the invention, methods for attaching a sheet-like implant to a target tissue are disclosed. In some embodiments, the methods include the steps of providing a staple push rod carrying a staple, depressing the target tissue to form a depression therein, advancing a first fluke of the staple into tissue at a first side of the depression, and advancing a second fluke of the staple into tissue at a second side of the depression. In these embodiments, the staple includes first and second arms, each arm having proximal and distal ends. A bridge extends from the proximal end of the first arm to the proximal end of the second arm. A first fluke of the staple has a proximal end abutting the distal end of the first arm. A second fluke of the staple has a proximal end abutting the distal end of the second arm. The staple push rod of the device includes a shaft, a first stake and a second stake. Each stake has a distal portion and a proximal portion. A proximal end of the proximal portion of each stake is fixed to a distal end of the shaft. The distal portion of the first stake extends into a first passage defined by the first fluke of the staple. The distal portion of the second stake extends into a second passage defined by the second fluke of the staple. The stakes are biased to assume a bow-like shape such that an intermediate portion of the staple extends tautly between the first stake and the second stake.

In some embodiments, the first side of the depression and the second side of the depression are generally opposite each other. The intermediate portion of the staple may be pulled taut when the first end is advanced into tissue at the first side of the depression and the second end of the staple is advanced into tissue at the second side of the depression. In some embodiments, the intermediate portion of the staple is positioned below a tissue plane when the first end is advanced into tissue at the first side of the depression and the second end of the staple is advanced into tissue at the second side of the depression. In some embodiments, the tissue plane is defined by an outer surface of a remainder of the target tissue, and the remainder of the target tissue does not include the depression.

In some embodiments, the method further comprises the step of providing a sheath having a proximal end, a distal end and a lumen extending therebetween. The step of depressing the target tissue to form a depression therein comprises pushing on the target tissue with the distal end of the sheath.

According to aspects of the invention, methods for attaching a sheet-like implant to a target tissue are disclosed. In some embodiments, the method includes the steps of providing a staple push rod carrying a staple, advancing a first fluke of the staple in a first direction, advancing a second fluke of the staple in a second direction that is generally opposite the first direction, moving the first end and the second ends away from each other, and pulling an intermediate portion of the staple taut between the first end and the second end. In these embodiments, the staple comprises first and second arms, each arm having proximal and distal ends. A bridge extends from the proximal end of the first aim to the proximal end of the second arm. A first fluke of the staple has a proximal end abutting the distal end of the first arm. A second fluke of the staple has a proximal end abutting the distal end of the second arm. The staple push rod of the device includes a shaft, a first stake and a second stake. Each stake has a distal portion and a proximal portion. A proximal end of the proximal portion of each stake is fixed to a distal end of the shaft. The distal portion of the first stake extends into a first passage defined by the first fluke, and the distal portion of the second stake extends into a second passage defined by the second fluke. The stakes are biased to assume a bow-like shape such that an intermediate portion of the staple extends tautly between the first stake and the second stake.

In some embodiments, the method further includes the step of advancing the first fluke in a distal direction through the sheet-like implant. This step may be performed before the step of advancing the first fluke of the staple in the first direction. In some embodiments, the distal direction is a generally parallel to a longitudinal axis of the shaft. In some embodiments, the distal direction is an axial direction relative to the shaft and the first direction is a lateral direction relative to the shaft.

Further aspects of the invention will become apparent upon review of the Detailed Description of the Invention with reference to the following drawings.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

As used herein, the term "tissue" refers to soft tissue, such as a tendon, and/or bone tissue, depending on the context in which it is used.

Figure 1:
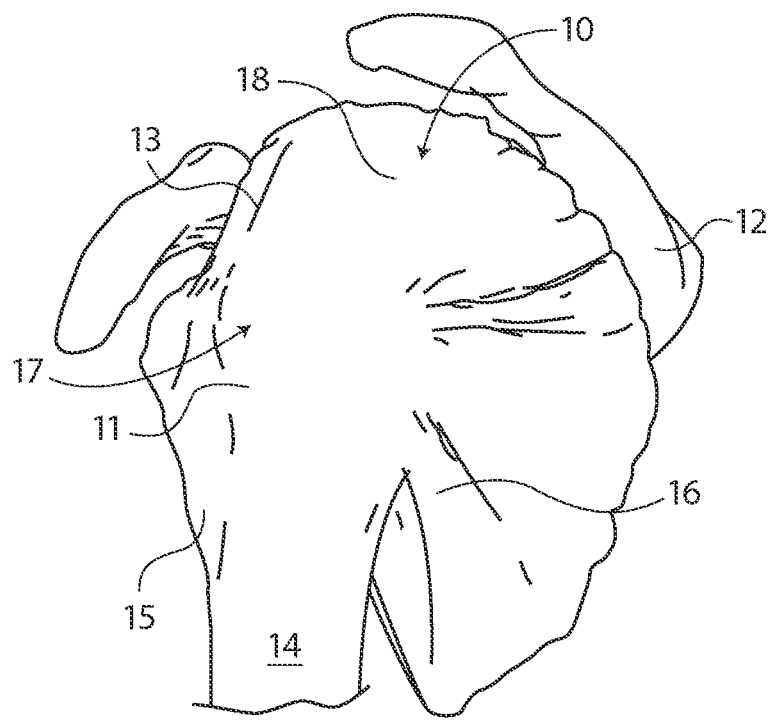
FIG. 1 is a simplified perspective view of the human rotator cuff and associated anatomical structure.
Figure 2:
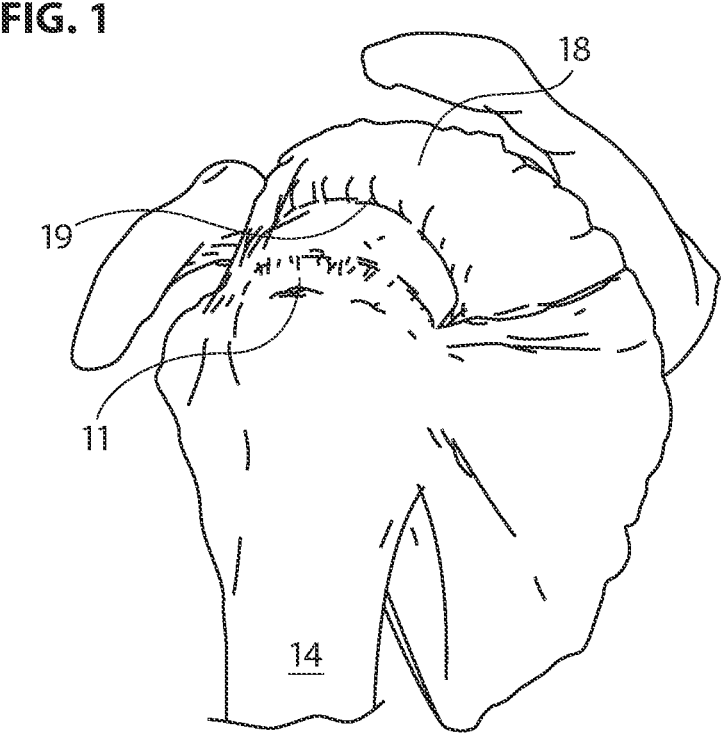
FIG. 2 is a schematic depiction of a full thickness tear in the supraspinatus tendon of the rotator cuff of FIG. 1.
Figure 3:
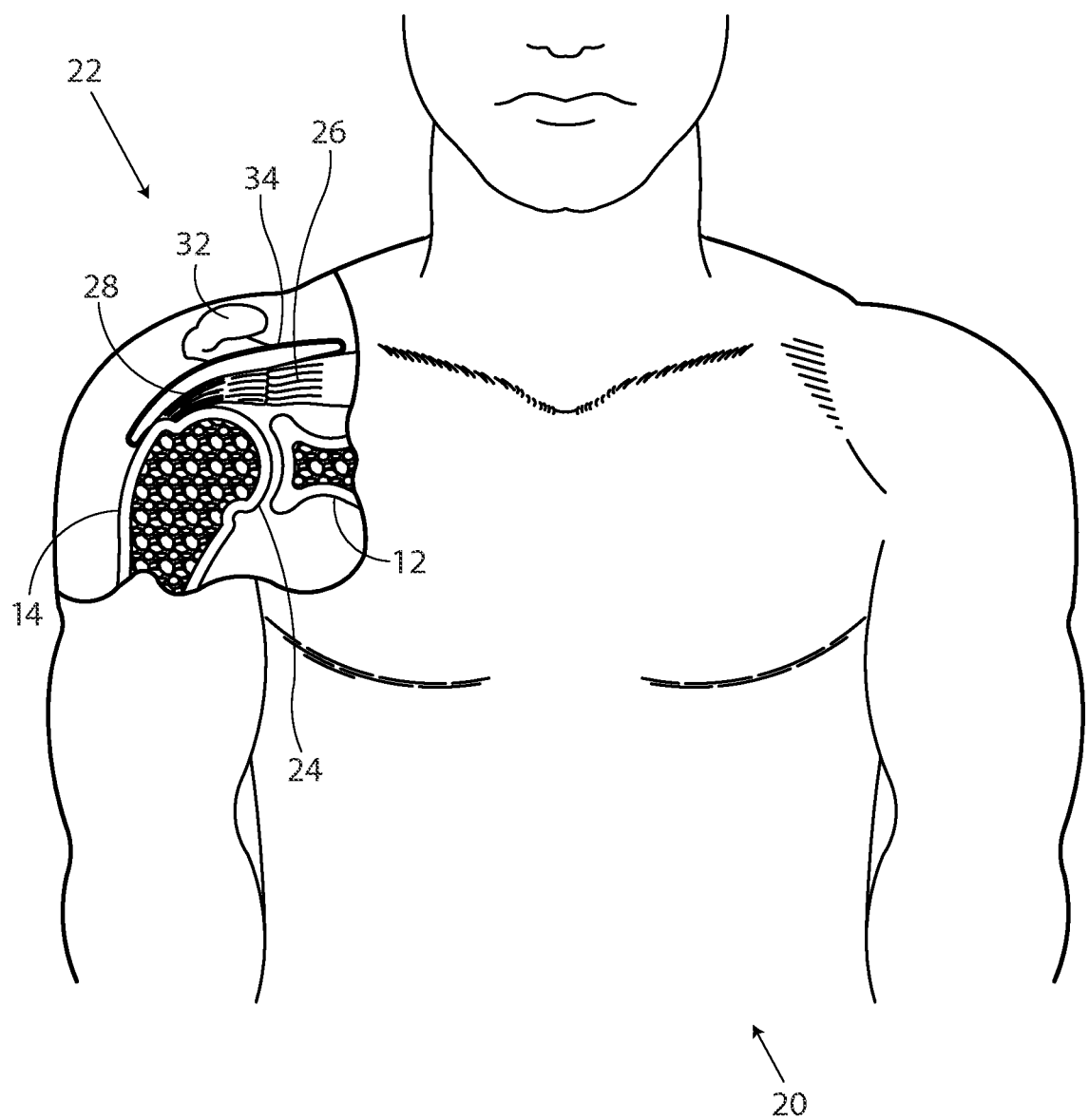
FIG. 3 is a stylized anterior view of a patient with a shoulder of patient being shown in cross-section for purposes of illustration.

FIG. 3 is a stylized anterior view of a patient 20. For purposes of illustration, a shoulder 22 of patient 20 is shown in cross-section in FIG. 3. Shoulder 22 includes a humerus 14 and a scapula 12. In FIG. 3, a head 24 of humerus 14 can be seen mating with a glenoid fossa of scapula 12 at a glenohumeral joint. With reference to FIG. 3, it will be appreciated that the glenoid fossa comprises a shallow depression in scapula 12. The movement of humerus 14 relative to scapula 12 is controlled by a number of muscles including: the deltoid, the supraspinatus, the infraspinatus, the subscapularis, and the teres minor. For purposes of illustration, only the supraspinatus 26 is shown in FIG. 3.

With reference to FIG. 3, it will be appreciated that a distal tendon 28 of the supraspinatus 26 meets humerus 14 at an insertion point. Scapula 12 of shoulder 22 includes an acromium 32. In FIG. 3, a subacromial bursa 34 is shown extending between acromium 32 of scapula 12 and head 24 of humerus 14. In FIG. 3, subacromial bursa 34 is shown overlaying supraspinatus 26. Subacromial bursa 34 is one of the hundreds of bursae found in the human body. Each bursa comprises a fluid filled sac. The presence of these bursae in the body reduces friction between bodily tissues. Injury and/or infection of the bursa can cause it to become inflamed. This condition is sometimes referred to as bursitis.

The exemplary methods and apparatus described herein may be used to fix tendon repair implants to various target tissues. For example, a tendon repair implant may be fixed to one or more tendons associated with an articulating joint, such as the glenohumeral joint. The tendons to be treated may be torn, partially torn, have internal micro-tears, be untorn, and/or be thinned due to age, injury or overuse. Applicants believe that the methods and apparatus of the present application and related devices may provide very beneficial therapeutic effect on a patient experiencing joint pain believed to be caused by partial thickness tears and/or internal microtears. By applying a tendon repair implant early before a full tear or other injury develops, the implant may cause the tendon to thicken and/or at least partially repair itself, thereby avoiding more extensive joint damage, pain, and the need for more extensive joint repair surgery.

Figure 4:
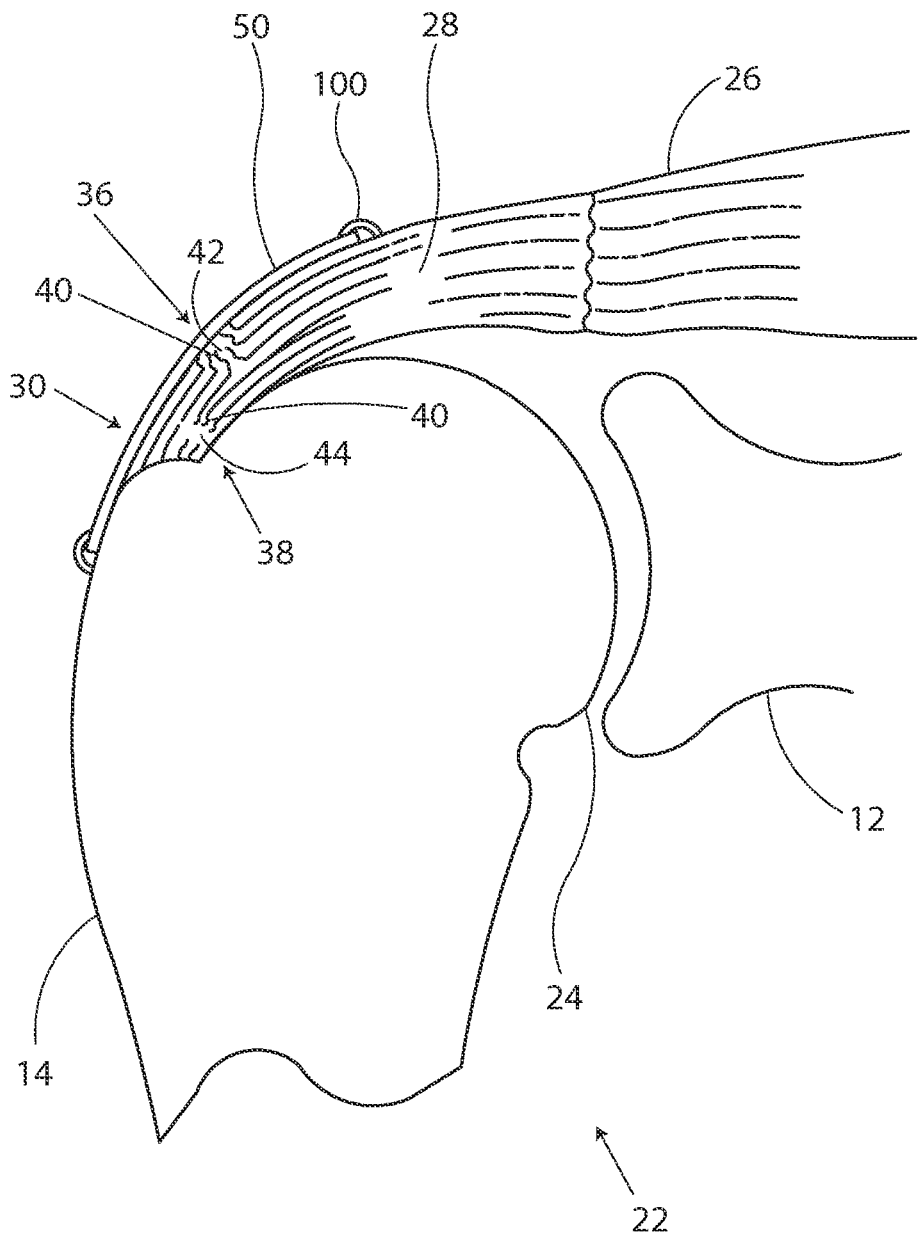
FIG. 4 is a stylized anterior view of a shoulder including a humerus and a scapula. The head of the humerus is shown mating with the glenoid fossa of the scapula at a glenohumeral joint and a sheet-like material is fixed to the tendon.

FIG. 4 is a stylized anterior view of a shoulder 22 including a humerus 14 and a scapula 12. In FIG. 4, a head 24 of humerus 14 is shown mating with a glenoid fossa of scapula 12 at a glenohumeral joint. A supraspinatus 26 is also shown in FIG. 4. This muscle (along with others) control the movement of humerus 14 relative to scapula 12. A distal tendon 28 of supraspinatus 26 meets humerus 14 at an insertion point 30.

In the embodiment of FIG. 4, distal tendon 28 includes a first damaged portion 36. A number of loose tendon fibers 40 in first damaged portion 36 are visible in FIG. 4. First damaged portion 36 includes a first tear 42 extending partially through distal tendon 28. First tear 42 may therefore be referred to as a partial thickness tear. With reference to FIG. 4, it will be appreciated that first tear 42 begins on the side of distal tendon 28 facing the subacromial bursa (shown in the previous figure) and ends midway through distal tendon 28. Accordingly, first tear 42 may be referred to as a bursal side tear.

With reference to FIG. 4, it will be appreciated that distal tendon 28 includes a second damaged portion 38 located near insertion point 30. In the embodiment of FIG. 4, second damaged portion 38 of distal tendon 28 has become frayed and a number of loose tendon fibers 40 are visible in FIG. 4. Second damaged portion 38 of distal tendon 28 includes second tear 44. With reference to FIG. 4, it will be appreciated that second tear 44 begins on the side of distal tendon 28 facing the humerus 14. Accordingly, second damaged portion 38 may be referred to as an articular side tear.

In the embodiment of FIG. 4, a sheet-like implant 50 has been placed over the bursal side of distal tendon 28. With reference to FIG. 4, it will be appreciated that sheet-like implant 50 extends over insertion point 30, first tear 42 and second tear 44. Some useful methods in accordance with this detailed description may include placing a tendon repair implant on the bursal side of a tendon regardless of whether the tears being treated are on the bursal side, articular side or within the tendon. In some cases the exact location and nature of the tears being treated may be unknown. A tendon repair implant may be applied to the bursal side of a tendon to treat shoulder pain that is most likely caused by one or more partial thickness tears in the tendon. In the embodiment of FIG. 4, sheet-like implant 50 is fixed to distal tendon 28 and to humerus 14 by a plurality of staples 100, as described in detail herein.

Figure 5:
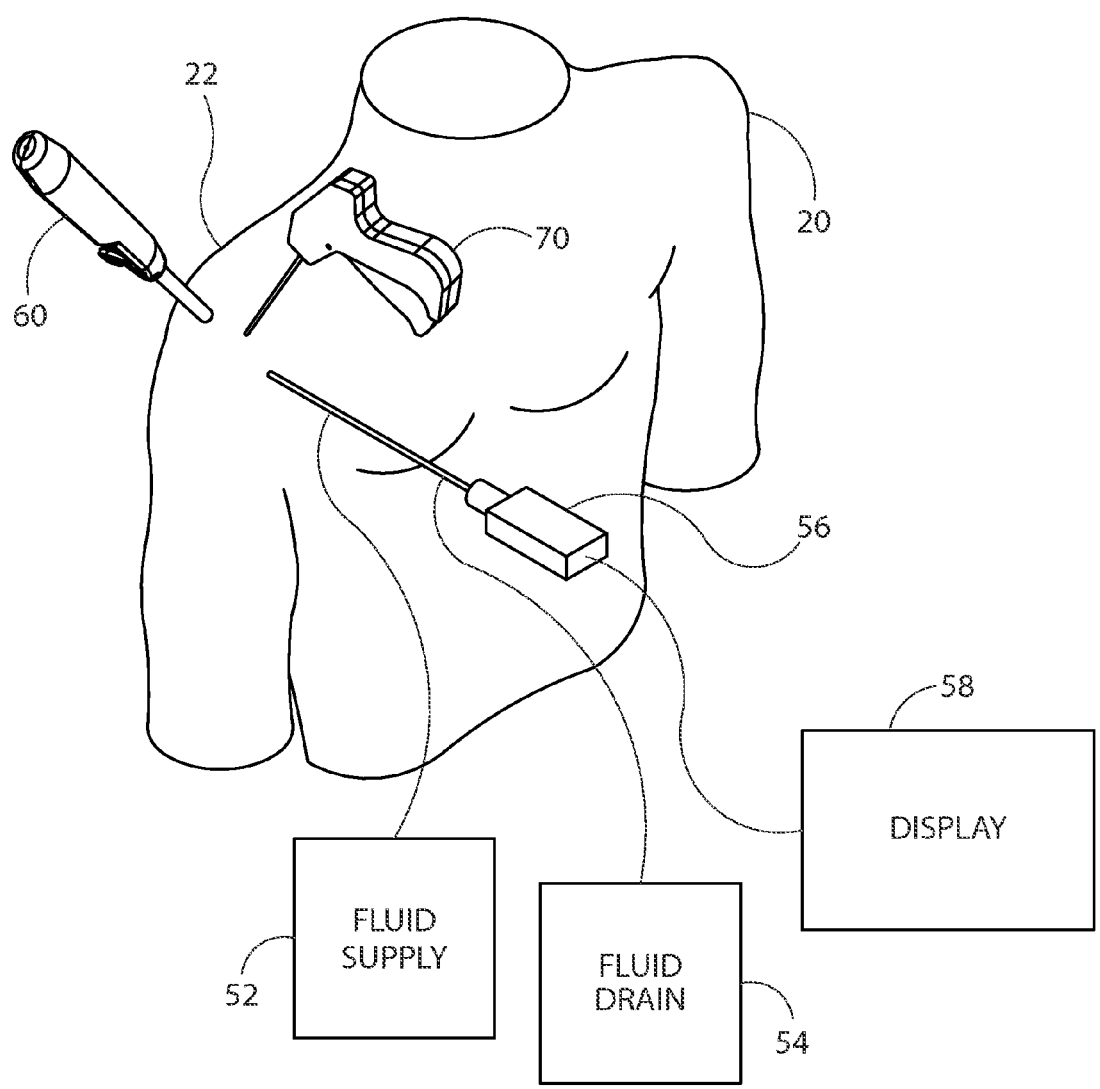
FIG. 5 is a stylized perspective view illustrating an exemplary procedure for treating a shoulder of a patient.

FIG. 5 is a stylized perspective view illustrating an exemplary procedure for treating a shoulder 22 of a patient 20. The procedure illustrated in FIG. 5 may include, for example, fixing tendon repair implants to one or more tendons of shoulder 22. The tendons treated may be torn, partially torn, have internal micro-tears, be untorn, and/or be thinned due to age, injury or overuse.

Shoulder 22 of FIG. 5 has been inflated to create a cavity therein. In the exemplary embodiment of FIG. 5A, a fluid supply 52 is pumping a continuous flow of saline into the cavity. This flow of saline exits the cavity via a fluid drain 54. A camera 56 provides images from inside the cavity. The images provided by camera 56 may be viewed on a display 58.

Camera 56 may be used to visually inspect the tendons of shoulder 22 for damage. A tendon repair implant in accordance with this disclosure may be fixed to a bursal surface of the tendon regardless of whether there are visible signs of tendon damage. Applicants believe that the methods and apparatus of the present application and related devices may provide very beneficial therapeutic effect on a patient experiencing joint pain believed to be caused by internal microtears, but having no clear signs of tendon tears. By applying a tendon repair implant early before a full tear or other injury develops, the implant may cause the tendon to thicken and/or at least partially repair itself, thereby avoiding more extensive joint damage, pain, and the need for more extensive joint repair surgery.

A delivery system 60 can be seen extending from shoulder 22 in FIG. 5. Delivery system 60 comprises a sheath that is fixed to a handle. The sheath defines a lumen and a distal opening fluidly communicating the lumen. In the embodiment of FIG. 5, the distal opening of the sheath has been placed in fluid communication with the cavity created in shoulder 22.

A tendon repair implant is at least partially disposed in the lumen defined by the sheath of delivery system 60. Delivery system 60 can be used to place the tendon repair implant inside shoulder 22. Delivery system 60 can also be used to hold the tendon repair implant against the tendon. In some embodiments, the tendon repair implant is folded into a compact configuration when inside the lumen of the sheath. When this is the case, delivery system 60 may be used to unfold the tendon repair implant into an expanded shape.

The tendon repair implant may be fixed to the tendon while it is held against the tendon by delivery system 60. Various attachment elements may be used to fix the tendon repair implant to the tendon. Examples of attachment elements that may be suitable in some applications include sutures, tissue anchors, bone anchors, and staples. In the exemplary embodiment of FIG. 5, the shaft of a fixation tool 70 is shown extending into shoulder 22. In one exemplary embodiment, fixation tool 70 is capable of fixing the tendon repair implant to the tendon with one or more staples while the tendon repair implant is held against the tendon by delivery system 60.

Figure 6:
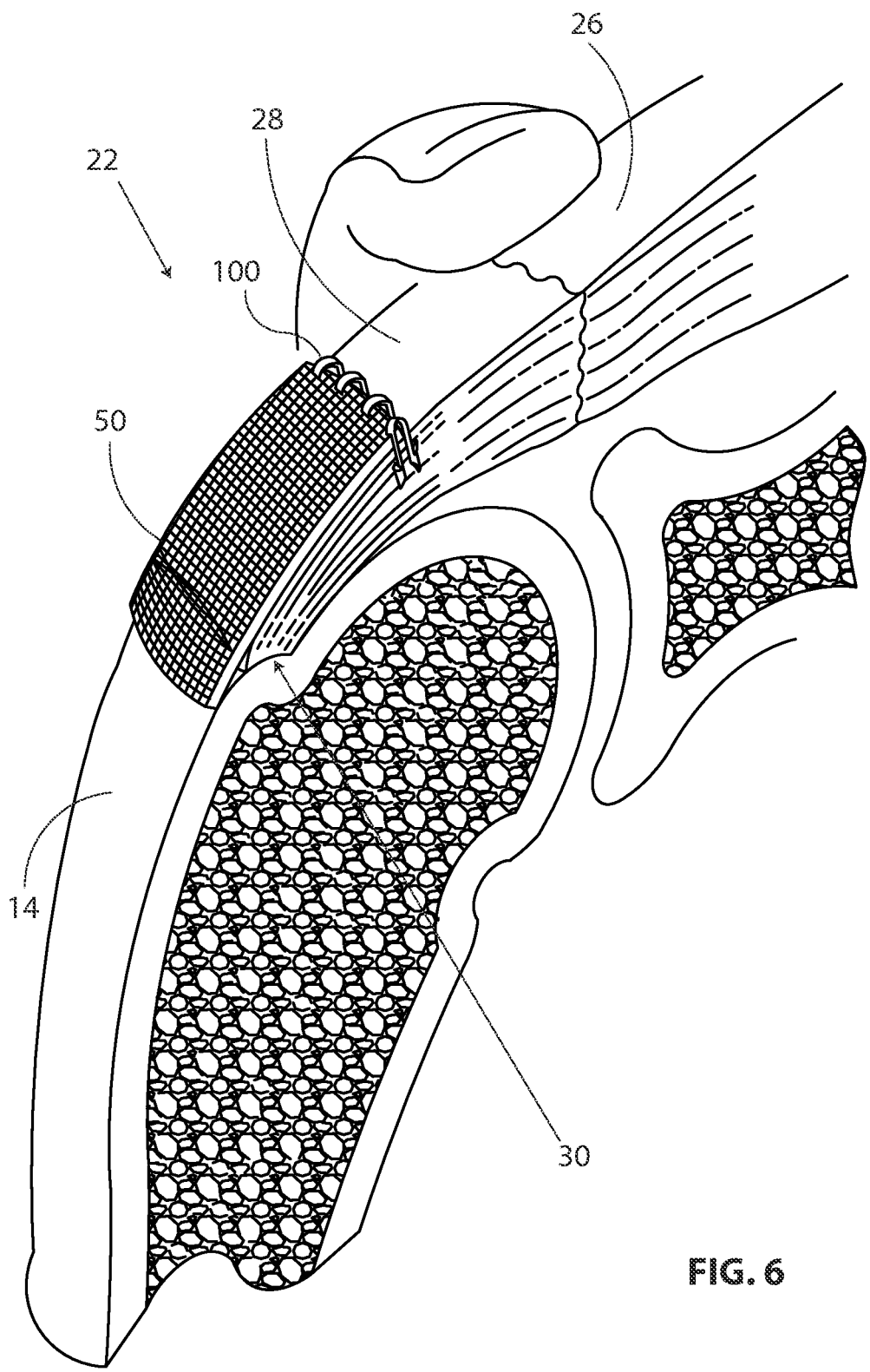
FIG. 6 is a stylized perspective view of a shoulder including a supraspinatus having a distal tendon with a sheet-like material fixed thereto. A proximal end of the supraspinatus is fixed to the scapula and the distal tendon of the supraspinatus is fixed to the humerus.

FIG. 6 is a stylized perspective view of a shoulder 22 including a supraspinatus 26 having a distal tendon 28. With reference to FIG. 6, it will be appreciated that a tendon repair implant 50 has been fixed to a surface of distal tendon 28. Tendon repair implant 50 may comprise, for example, various sheet-like structures without deviating from the spirit and scope of the present detailed description. In some useful embodiments, the sheet-like structure may comprise a plurality of fibers. The fibers may be interlinked with one another. When this is the case, the sheet-like structure may comprise a plurality of apertures comprising the interstitial spaces between fibers. Various processes may be used to interlink the fibers with one another. Examples of processes that may be suitable in some applications including weaving, knitting, and braiding. In some embodiment, the sheet-like structure may comprise a laminate including multiple layers of film with each layer of film defining a plurality of micro-machined or formed holes. The sheet-like structure of the tendon repair implant may also comprise a plurality of electro-spun nanofiber filaments forming a composite sheet. Additionally, the sheet-like structure may comprise a synthetic sponge material that defines a plurality of pores. The sheet-like structure may also comprise a reticulated foam material. Reticulated foam materials that may be suitable in some applications are available from Biomerix Corporation of Freemont, Calif. which identifies these materials using the trademark BIOMATERIAL™.

Various attachment elements may be used to fix tendon repair implant 50 to distal tendon 28 without deviating from the spirit and scope of this detailed description. Examples of attachment elements that may be suitable in some applications include sutures, tissue anchors, bone anchors, and staples. In the exemplary embodiment of FIG. 6, a plurality of staples 100 are fixing tendon repair implant 50 to distal tendon 28. In some exemplary methods, a plurality of staples 100 may be applied using a fixation tool. The fixation tool may then be withdrawn from the body of the patient. Distal tendon 28 meets humerus 14 at an insertion point 30. With reference to FIG. 6, it will be appreciated that sheet-like implant 50 extends over insertion point 30. Tendon repair implant may be applied to distal tendon 28, for example, using the procedure illustrated in the previous figure.

Figure 7C:
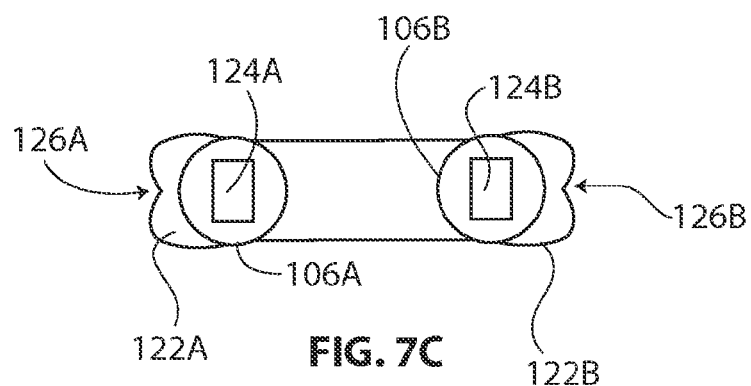
FIG. 7A, FIG. 7B, and FIG. 7C are multiple plan views illustrating an exemplary staple in accordance with the present detailed description.
Figure 7A:
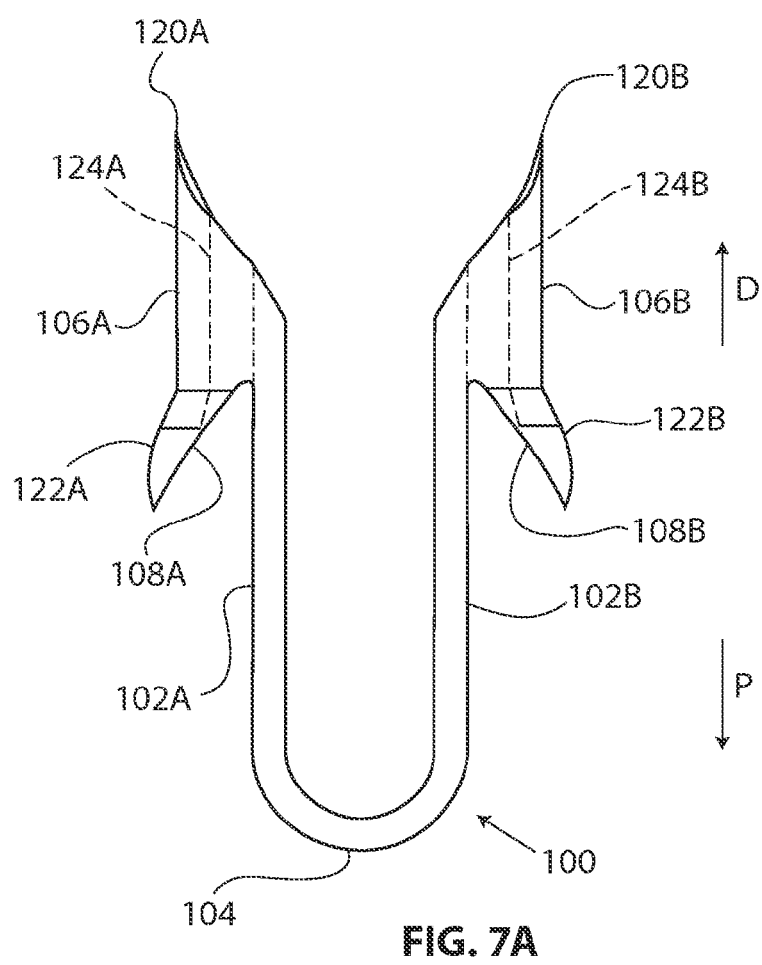
Figure 7B:
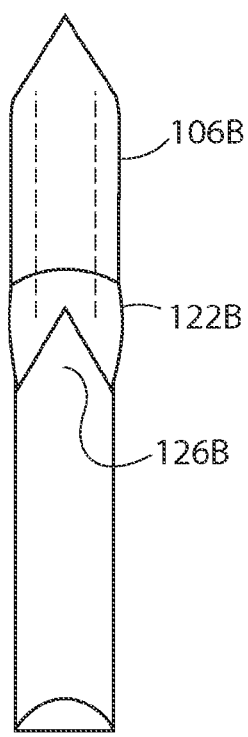

FIG. 7A, FIG. 7B, and FIG. 7C are multiple plan views illustrating an exemplary staple 100 in accordance with the present detailed description. FIG. 7A, FIG. 7B, and FIG. 7C may be collectively referred to as FIG. 7. A proximal direction is illustrated with an arrow P in FIG. 7. A distal direction is illustrated with a second arrow D in FIG. 7.

Staple 100 comprises a first arm 102A, a second arm 102B, and a bridge 104 extending from the proximal end of first arm 102A to the proximal end of second arm 102B. The distal end of first arm 102A abuts the proximal end of a first fluke 106A. Similarly, the distal end of second arm 102B abuts the proximal end of a second fluke 106B. In FIG. 7, first fluke 106A and second fluke 106B are shown extending distally from first arm 102A and second arm 102B, respectively. With reference to FIG. 7, it will be appreciated that first fluke 106A has a lateral extent that is larger than a lateral extent of first arm 102A. First fluke 106A is mounted eccentrically to first arm 102A in the embodiment of FIG. 7. Second fluke 106B is mounted eccentrically to second arm 102B and second fluke 106B has a lateral extent that is larger than a lateral extent of second arm 102B. First fluke 106A includes a first proximal surface 108A projecting at an outward angle in a proximal direction away from the distal end of first arm 102A. Second fluke 106B includes a second proximal surface 108B projecting at an outward angle in a proximal direction away from the distal end of second arm 102B.

With reference to FIG. 7A, it will be appreciated that first fluke 106A includes a first point 120A and a first barb 122A. Second fluke 106B includes a second point 120B and a second barb 122B. In FIG. 7, first point 120A and second point 120B are shown generally pointing in the distal direction indicated by arrow D. Also in FIG. 7, first barb 122A and second barb 122B are shown generally pointing in the proximal direction indicated by arrow P.

With reference to FIG. 7A it will be appreciated that first fluke 106A defines a first passageway 124A and second fluke 106B defines a second passageway 124B. In the exemplary embodiment of FIG. 7, first passageway 124A extends through first fluke 106A and second passageway 124B extends through second fluke 106B. It will be appreciated, however, that first passageway 124A may extend through other portions of staple 100 in some embodiments. Similarly, second passageway 124B may extend through other portions of staple 100 in some embodiments. With reference to FIG. 7B it will be appreciated that, first passageway 124A and second passageway 124B each have a generally square cross-sectional shape. It will be appreciated, however, that first passageway 124A and second passageway 124B may have various cross-sectional shapes without deviating from the spirit and scope of the present detailed description. It will also be appreciated that each passageway can extend partially through the length of each fluke rather than completely through the length of each fluke. When this is the case, each passageway will provide a blind hole rather than a through hole.

With reference to FIG. 7C, it will be appreciated that first barb 122A of first fluke 106A defines a first notch 126A. In the exemplary embodiment of FIG. 7, first notch 126A divides first barb 122A into a first sub-barb and a second sub-barb. Second barb 122B of second fluke 106B defines a second notch 126B. In the exemplary embodiment of FIG. 7, second notch 126B divides second barb 122B into a first sub-barb and a second sub-barb.

Figure 8:
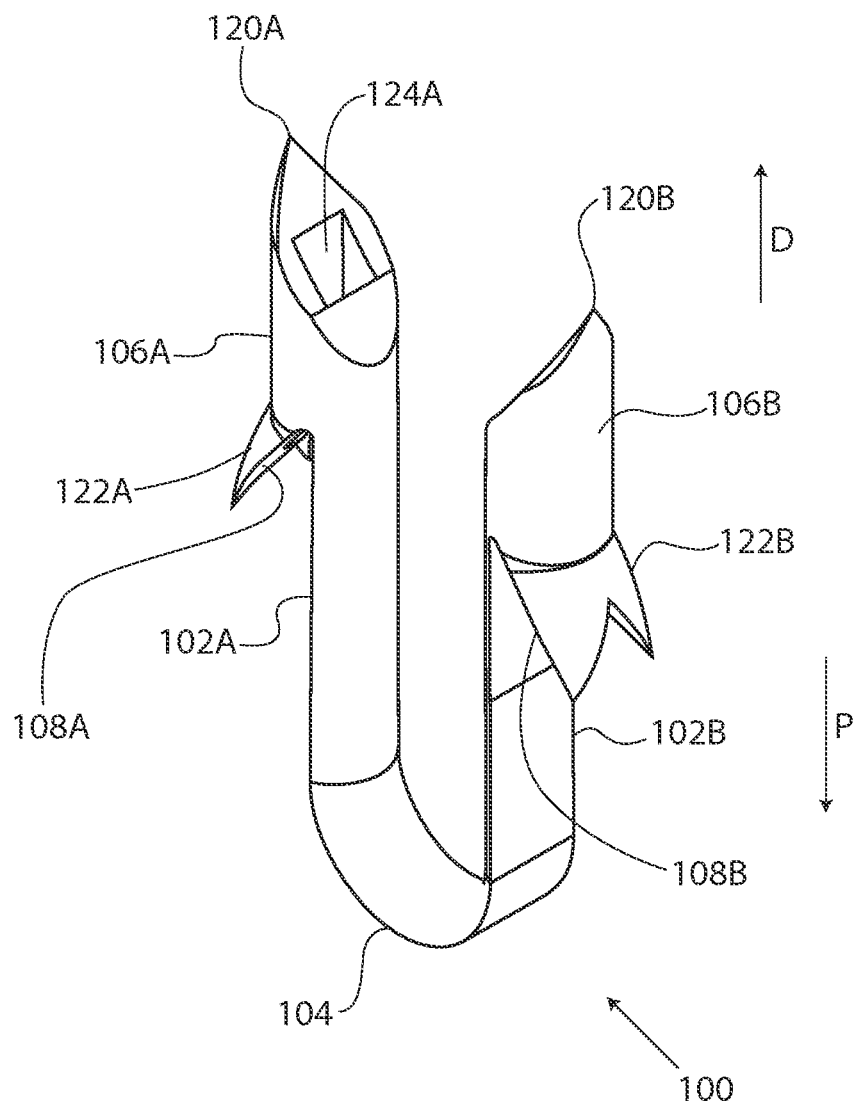
FIG. 8 is a perspective view further illustrating the staple shown in the previous figure.

FIG. 8 is a perspective view showing staple 100 shown in the previous figure. Staple 100 comprises a first arm 102A, a second arm 102B, and a bridge 104 extending from the proximal end of first arm 102A to the proximal end of second arm 102B. The distal end of first arm 102A abuts the proximal end of a first fluke 106A. With reference to FIG. 8 it will be appreciated that first fluke 106A defines a first passageway 124A. In the exemplary embodiment of FIG. 8, first passageway 124A has a generally square cross-sectional shape. It will be appreciated, however, that first passageway 124A may have various cross-sectional shapes without deviating from the spirit and scope of the present detailed description.

A second fluke 106B extends distally from second arm 102B with the proximal end of second fluke 106B abutting the distal end of second arm 102B. With reference to FIG. 8, it will be appreciated that second fluke 106B has a lateral extent that is larger than a lateral extent of second arm 102B. Second fluke 106B is mounted eccentrically to second arm 102BA in the embodiment of FIG. 8. Similarly, first fluke 106A is mounted eccentrically to first arm 102A and first fluke 106A has a lateral extent that is larger than a lateral extent of first arm 102A.

A proximal direction is illustrated with an arrow P in FIG. 8. A distal direction is illustrated with a second arrow D in FIG. 8. With reference to FIG. 8A, it will be appreciated that first fluke 106A of first arm 102A includes a first point 120A and a first barb 122A. Second fluke 106B includes a second point 120B and a second barb 122B. In FIG. 8, first point 120A and second point 120B are shown generally pointing in the distal direction indicated by arrow D. Also in FIG. 8, first barb 122A and second barb 122B are shown generally pointing in the proximal direction indicated by arrow P. With reference to FIG. 8, it will be appreciated that first fluke 106A includes a first proximal surface 108A projecting at an outward angle in a proximal direction away from the distal end of first arm 102A. Second fluke 106B includes a second proximal surface 108B projecting at an outward angle in a proximal direction away from the distal end of second arm 102B.

Figures 9A, 9B:
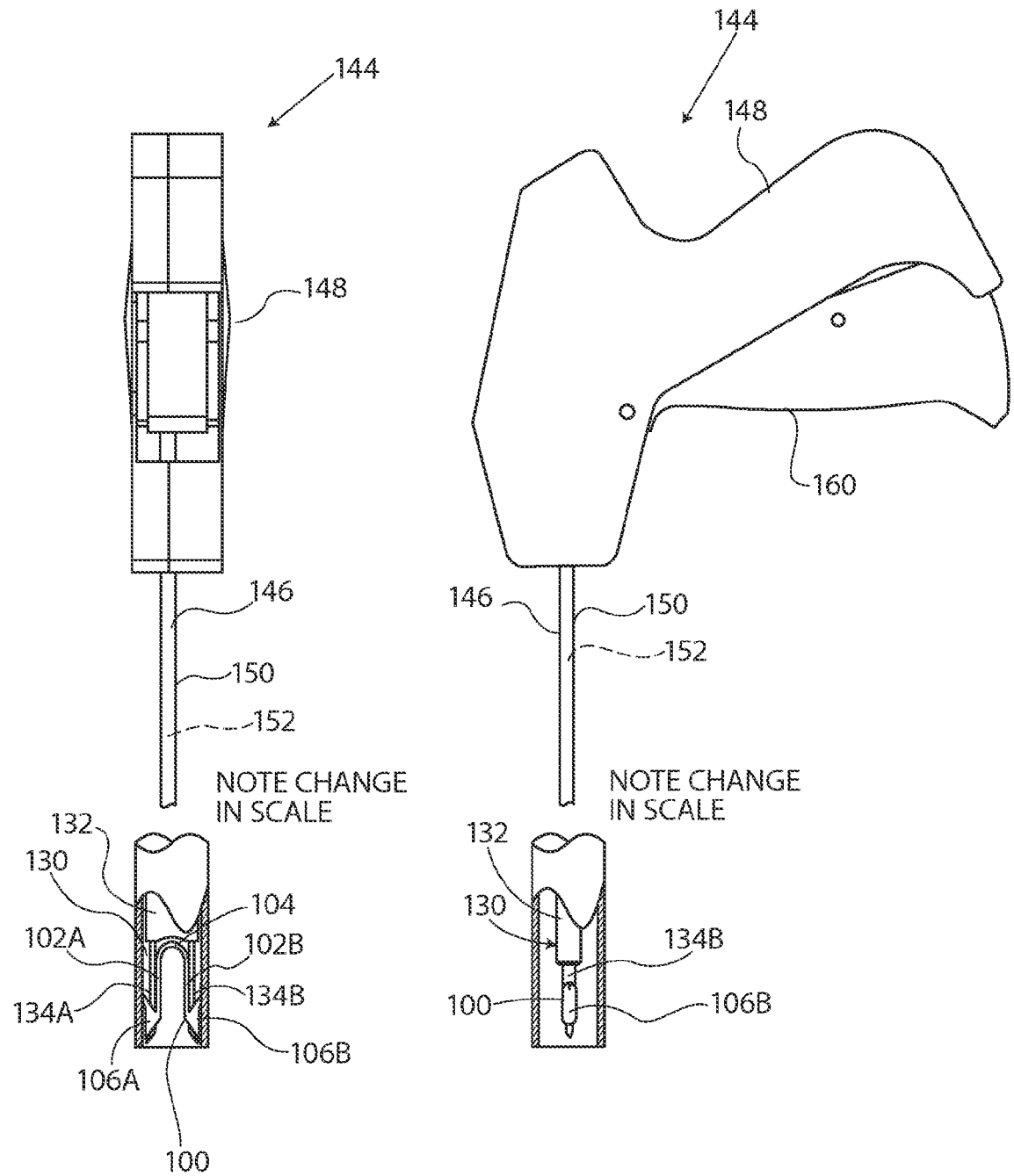
FIG. 9A and FIG. 9B illustrate multiple plan views of an exemplary fixation tool in accordance with the present detailed description.

FIG. 9A and FIG. 9B illustrate multiple plan views of an exemplary fixation tool 144 in accordance with the present detailed description. FIG. 9A and FIG. 9B may be referred to collectively as FIG. 9. It is customary to refer to multi-view projections using terms such as front view, top view, and side view. In accordance with this convention, FIG. 9A may be referred to as a top view of fixation tool 144 and FIG. 9B may be referred to as a side view of fixation tool 144. The terms top view and side view are used herein as a convenient method for differentiating between the views shown in FIG. 9. It will be appreciated that the elements shown in FIG. 9 may assume various orientations without deviating from the spirit and scope of this detailed description. Accordingly, the terms top view and side view should not be interpreted to limit the scope of the invention recited in the attached claims.

In the embodiment of FIG. 9, fixation tool 144 includes a fixation tool sheath 146 that is attached to a handle 148. Fixation tool sheath 146 comprises a wall 150 defining a lumen 152. In FIG. 9, a staple 100 can be seen residing in lumen 152 of fixation tool sheath 146. For purposes of illustration, a distal portion of fixation tool sheath 146 is enlarged in FIG. 9 to better show staple 100. Staple 100 comprises a first arm 102A, a second arm 102B, and a bridge 104 extending from the proximal end of first arm 102A to the proximal end of second arm 102B. The distal end of first arm 102A abuts the proximal end of a first fluke 106A. Similarly, the distal end of second arm 102B abuts the proximal end of a second fluke 106B. In FIG. 9, first fluke 106A and second fluke 106B are shown extending distally from first arm 102A and second arm 102B, respectively.

In the embodiment of FIG. 9, fixation tool 144 includes a staple push rod 130 that is slidingly received in lumen 152 defined by fixation tool sheath 146. Staple push rod 130 includes a shaft 132 and a pair of stakes 134 that are coupled to shaft 132. Stakes 134 include a first stake 134A and a second stake 134B. First stake 134A and second stake 134B each have a distal portion 138 and a proximal portion 140. In FIG. 9, the distal portion 138 of each stake 134 can be seen extending through a passageway defined by staple 100. In the embodiment of FIG. 9, a trigger 160 is pivotably coupled to handle 148 of fixation tool 144. Trigger 160 is operatively coupled to staple push rod 130. In operation, staple push rod 130 will be advanced and/or retracted in an axial direction when trigger 160 is pivoted relative to handle 148. With reference to FIG. 9, it will be appreciated that staple 100 is disposed on a distal portion of staple push rod 130. Accordingly, staple 100 can be moved distally and/or proximately by pivoting trigger 160 relative to handle 148 of fixation tool 144.

Figure 10:
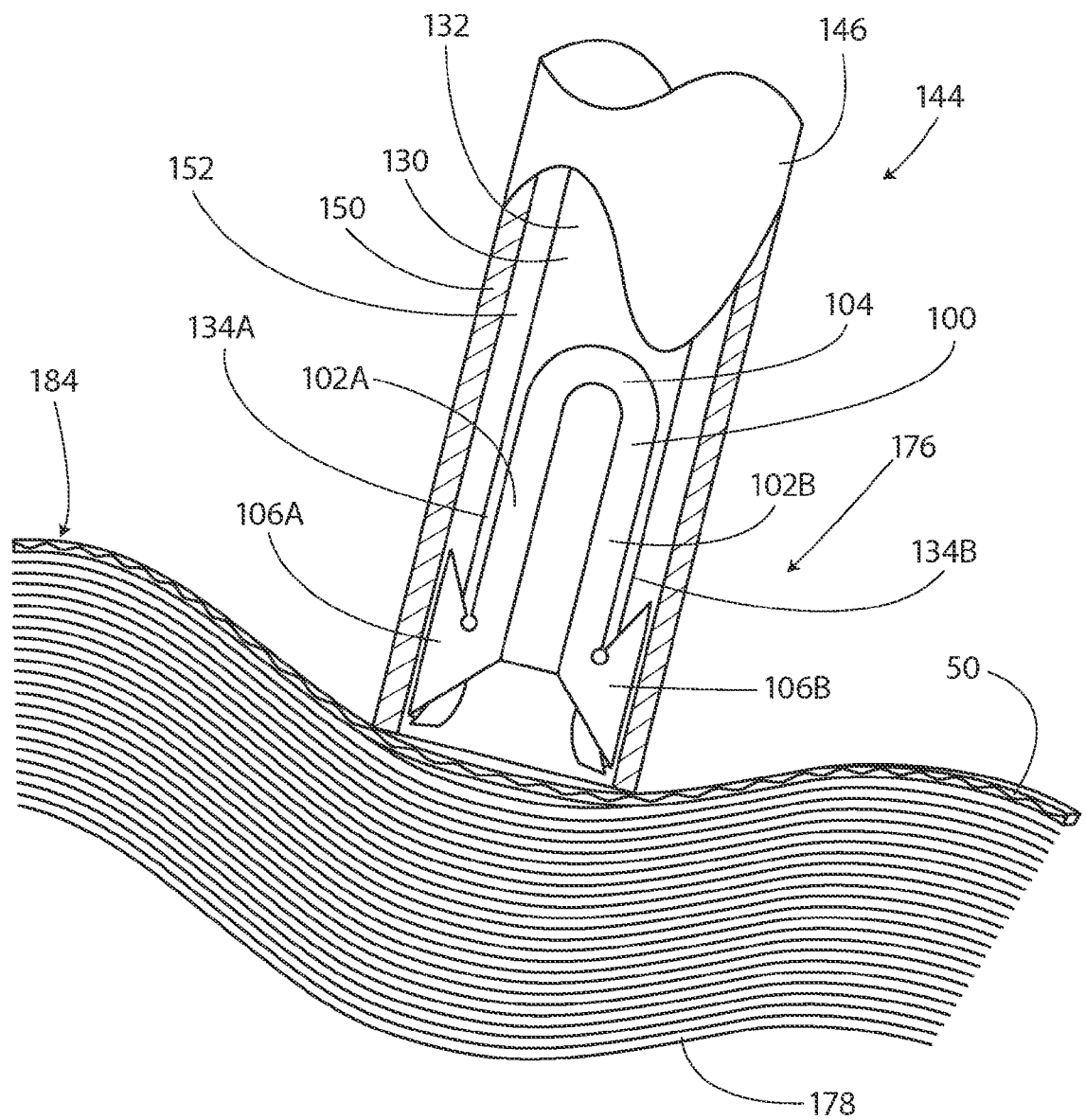
FIG. 10 is an enlarged plan view showing a distal portion of the fixation tool shown in the previous figure.

FIG. 10 is an enlarged plan view showing a distal portion of fixation tool 144. For purposes of illustration, a portion of fixation tool sheath 146 is cut-away in FIG. 10. Accordingly, staple 100 and staple push rod 130 can be seen residing in a distal portion of fixation tool sheath 146. In FIG. 10, the distal end of fixation tool sheath 146 is pushing against a sheet-like implant 50 and a target tissue 178. The pushing force applied by fixation tool 144 has caused a depression 176 to form in target tissue 178. Depression 176 lies below a plane defined by an outer surface 184 of the remainder of target tissue 178. The remainder of target tissue 178 is a portion of target tissue not including depression 176.

Fixation tool sheath 146 comprises a wall 150 defining a lumen 152. In FIG. 10, fixation tool sheath 146 is shown in partial cross-section. Accordingly, a staple 100 can be seen residing in lumen 152 of fixation tool sheath 146. Staple 100 comprises a first arm 102A, a second arm 102B, and a bridge 104 extending from the proximal end of first arm 102A to the proximal end of second arm 102B. The distal end of first arm 102A abuts the proximal end of a first fluke 106A. Similarly, the distal end of second arm 102B abuts the proximal end of a second fluke 106B. In FIG. 10, first fluke 106A and second fluke 106B are shown extending distally from first arm 102A and second arm 102B, respectively.

Fixation tool 144 of FIG. 10 includes a staple push rod 130 that is slidingly disposed in lumen 152 defined by fixation tool sheath 146. Staple push rod 130 includes a shaft 132 and a pair of stakes 134 that are coupled to shaft 132. Stakes 134 include a first stake 134A and a second stake 134B. In FIG. 10, a distal portion of each stake 134 can be seen extending through a passageway defined by staple 100.

Figure 11:
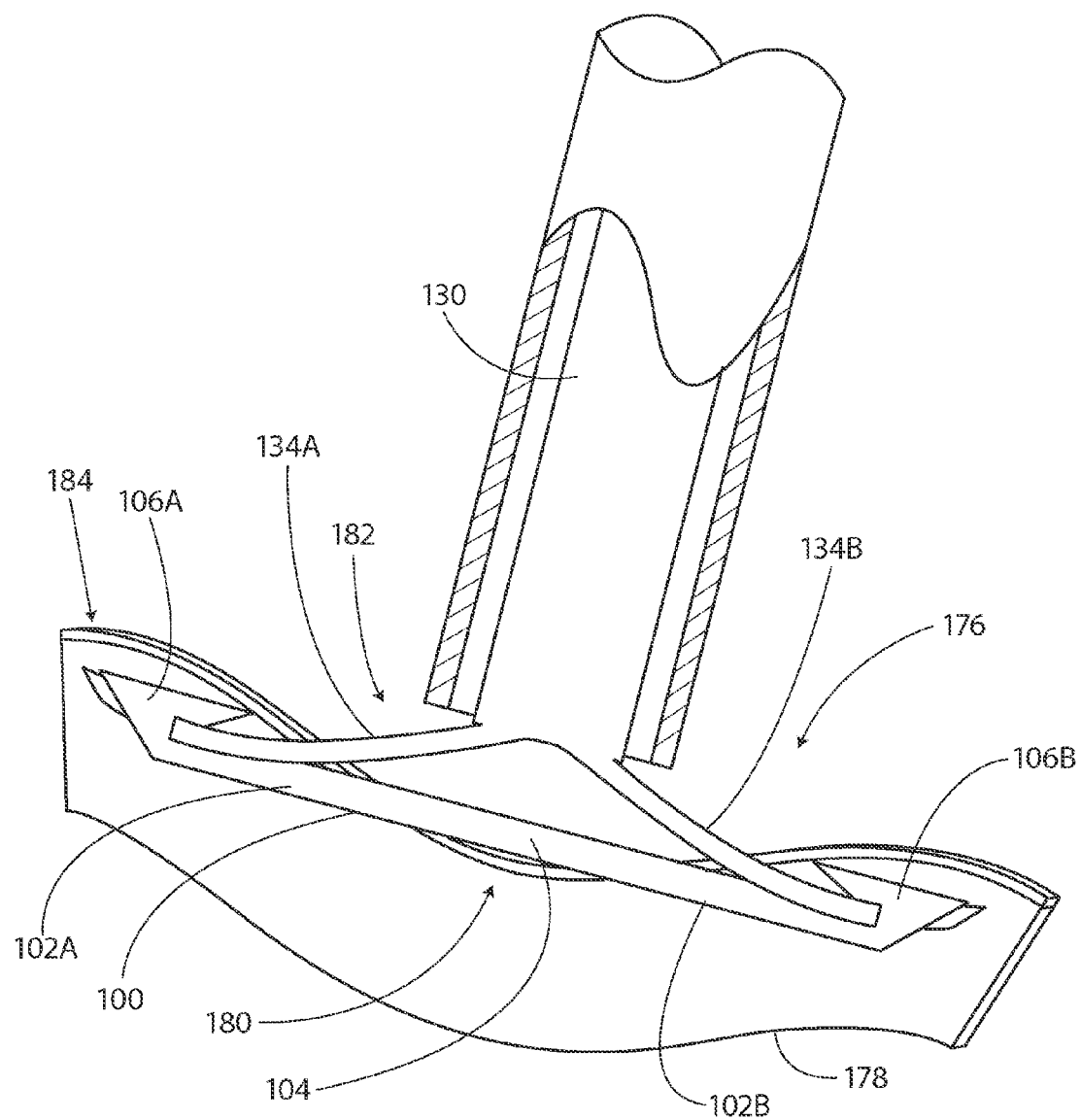
FIG. 11 is an additional plan view showing the target tissue shown in the previous figure.

FIG. 11 is an additional plan view showing target tissue 178 shown in the previous figure. In the embodiment of FIG. 11, first fluke 106B of staple 100 has been advanced into target tissue 178 at one side of depression 176. Second fluke 106B of staple 100 has been advanced into the tissue at a second side of depression 176. With reference to FIG. 11, it will be appreciated that first fluke 106A and second fluke 106B have been advanced in generally opposite directions. In FIG. 11 an intermediate portion 180 of staple 100 is shown extending along a generally straight path between first fluke 106A and second fluke 106B. In the exemplary embodiment of FIG. 11, intermediate portion 180 of staple 100 comprises first arm 102A, second arm 102B and bridge 104. Some methods in accordance with the present detailed disclosure include the step of pulling the intermediate portion of a staple taut between a first fluke and a second fluke.

With reference to FIG. 11, it will be appreciated that staple push rod 130 comprises a distal bow 182 formed of first stake 134A and second stake 134B. In FIG. 11, intermediate portion 180 of staple 100 is shown extending across distal bow 182 like a bowstring. In the embodiment of FIG. 11, intermediate portion 180 of staple 100 is disposed below a plane defined by an outer surface 184 of the remainder of target tissue 178. The remainder of target tissue 178 is the portion of target tissue 178 that does not include depression 176.

With reference to the two figures discussed immediately above, it will be appreciated that one exemplary method in accordance with the present detailed description may include providing a staple having a first fluke, a second fluke, and an intermediate portion extending therebetween; moving the first fluke and the second fluke away from one another; and pulling the intermediate portion taut between the first fluke and the second fluke.

An additional exemplary method may include providing a staple having a first fluke, a second fluke, and an intermediate portion extending therebetween; advancing the first fluke of the staple in a first direction; and advancing the second fluke of the staple in a second direction. In some cases the first direction and the second direction may be generally opposite directions.

Figure 12:
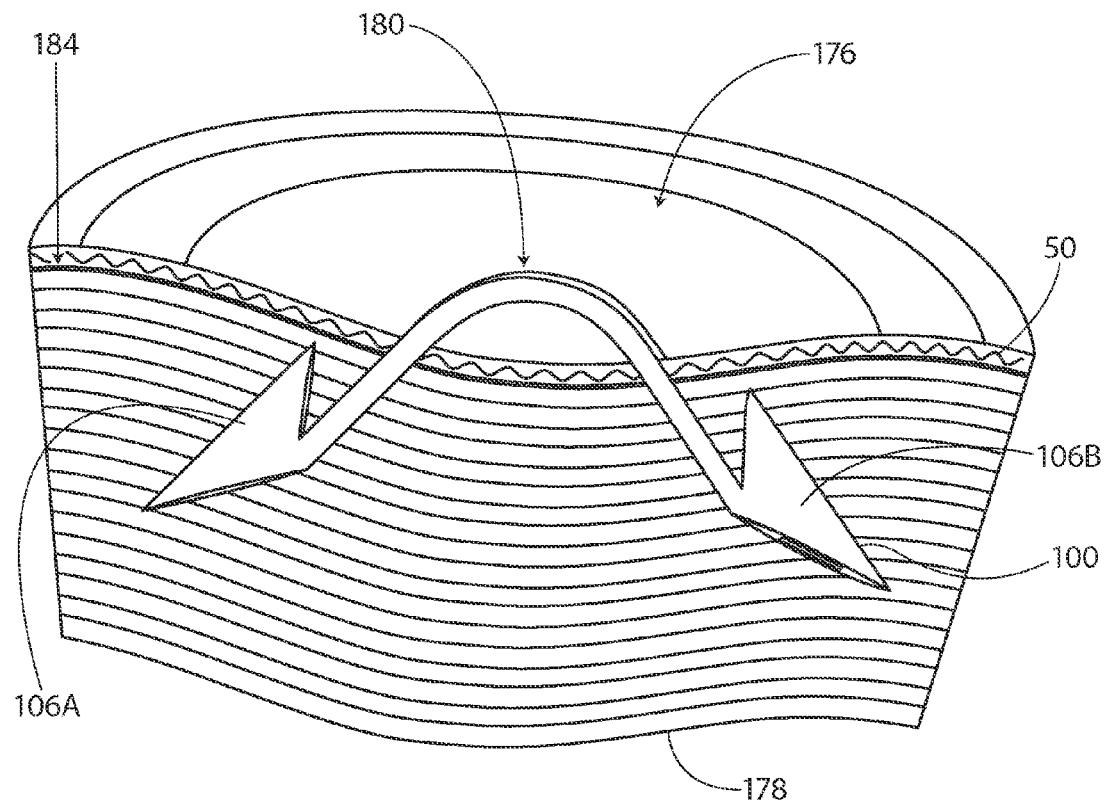
FIG. 12 is an additional plan view showing the target tissue illustrated in the previous figure.

FIG. 12 is an additional plan view showing the target tissue 178 illustrated in the previous figure. In the embodiment of FIG. 12, the first fluke 106A and the second fluke 106B of staple 100 are disposed in target tissue 178. In the exemplary embodiment of FIG. 12, a depression 176 is formed in target tissue 178. First fluke 106A is disposed near a first side of depression 176. Second fluke 106B is disposed near a second side of depression 176 that is generally opposite the first side of depression 176. With reference to FIG. 12, it will be appreciated that first fluke 106A and second fluke 106B are generally pointing away from each other.

In FIG. 12, an intermediate portion of staple 100 is shown extending between first fluke 106A and second fluke 106B. In the embodiment of FIG. 12, intermediate portion 180 of staple 100 is disposed below a plane defined by an outer surface 184 of the remainder of target tissue 178. The remainder of target tissue 178 is the portion of target tissue 178 that does not include depression 176. In the embodiment of FIG. 12, sheet-like implant 50 is fixed to target tissue 178 by staple 100.

A method of treating a target tissue in accordance with the present detailed description may include depressing the target tissue 178o form a depression therein. The first end of a staple may be advanced into tissue at a first side of the depression. The second end of the staple may be advanced into tissue at a second side of the depression. In some cases, the first side of the depression and the second side of the depression are generally opposite one another. An intermediate portion of the staple may be pulled taut when the first end is advanced into tissue at the first side of the depression and the second end of the staple is advanced into tissue at the second side of the depression. Additionally, the intermediate portion of the staple may be positioned below a tissue plane when the first end is advanced into tissue at the first side of the depression and the second end of the staple is advanced into tissue at the second side of the depression.

Figure 13:
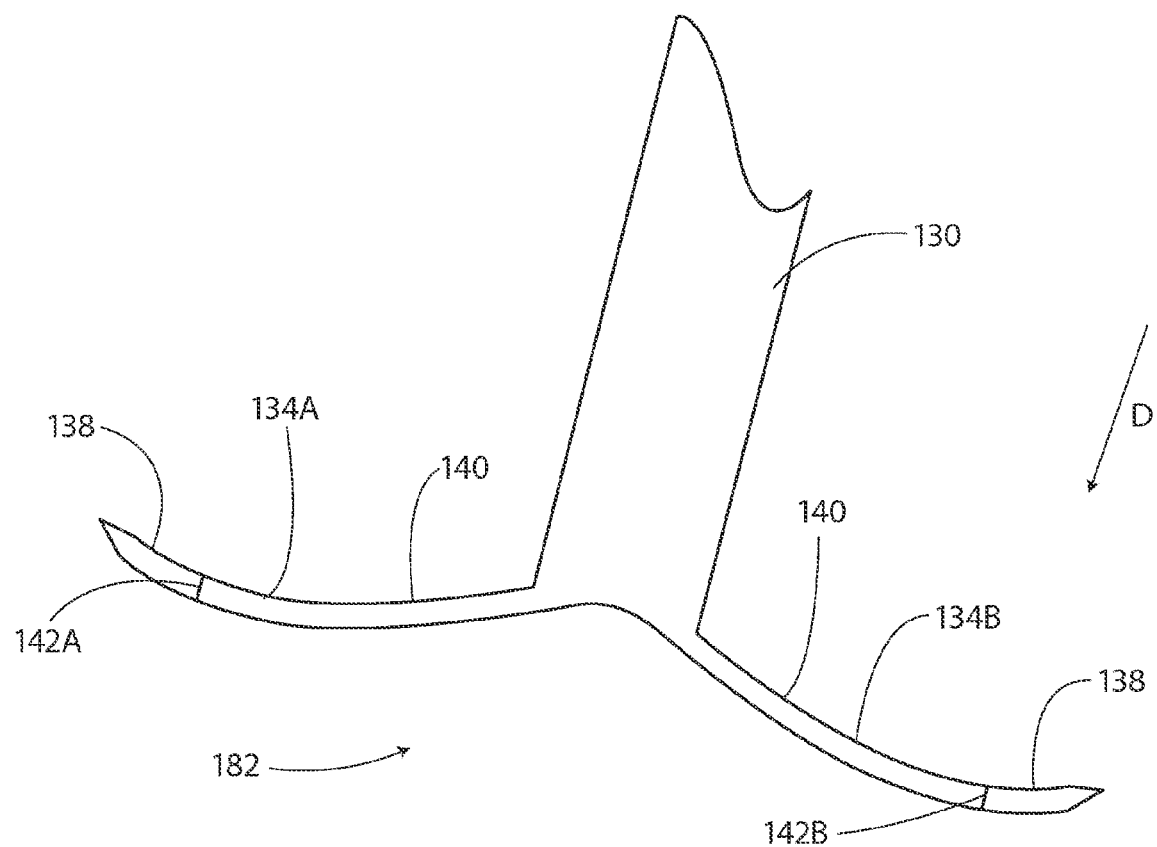
FIG. 13 is a plan view showing a staple push rod including a first stake and a second stake.

FIG. 13 is a plan view showing a staple push rod 130. In the embodiment of FIG. 13, staple push rod 130 comprises a first stake 134A and a second stake 134B. First stake 134A and second stake 134B form a distal bow 182. In the embodiment of FIG. 13, distal bow 182 has a shape analogous to the shape of recurve bows traditionally used in archery. In FIG. 13, first stake 134A and second stake 134B are in a substantially unstressed state. With reference to the figures discussed above, it will be appreciated that first stake 134A and second stake 134B can be resiliently urged to assume shapes other than the shape shown in FIG. 13. For example, first stake 134A and second stake 134B can be placed inside a fixation tool sheath.

In the embodiment of FIG. 13, each stake 134 has a distal portion 138 and a proximal portion 140. In some useful embodiments, each distal portion 138 is dimensioned to extend into a passage defined by a staple. In the embodiment of FIG. 13, each proximal portion 140 has a width larger than a width of each distal portion 138 so that a shoulder of each proximal portion 140 contacts a proximal surface of the staple to apply pushing forces thereto. First stake 134A comprises a first shoulder 142A and second stake 134B comprises a second shoulder 142B. In the embodiment of FIG. 13, proximal portion 140 of first stake 134A and the proximal portion 140 of second stake 134B diverge from one another as they extend in distal direction D away from shaft 132.

Figure 14:
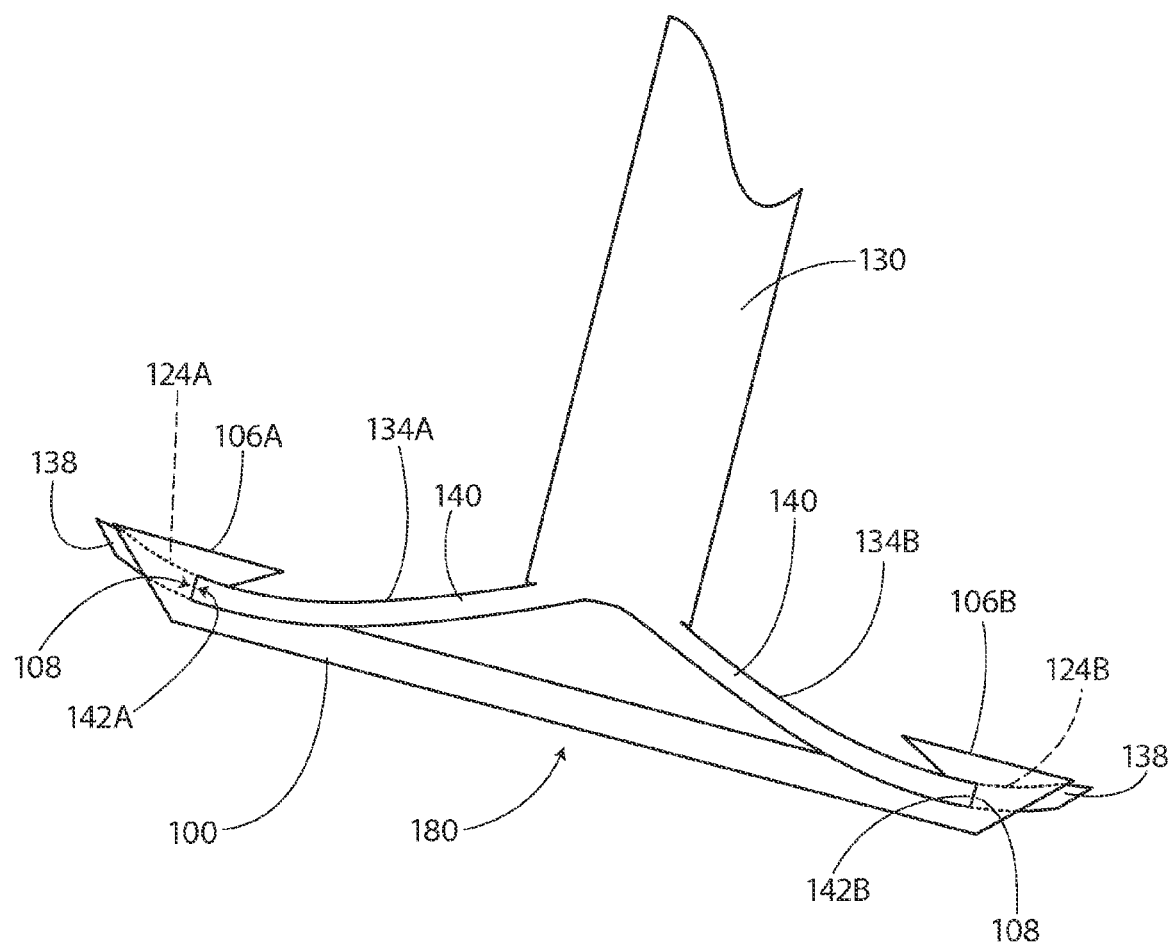
FIG. 14 is a plan view of an exemplary assembly in accordance with the present detailed description.

FIG. 14 is a plan view of an exemplary assembly in accordance with the present detailed description. The assembly of FIG. 14 comprises a staple push rod 130 and a staple 100. Staple push rod 130 comprises a first stake 134A and a second stake 134B. In FIG. 14, a distal portion 138 first stake 134A is shown extending into a first passageway 124A defined by a first fluke 106A of staple 100. Also in FIG. 14, a distal portion 138 of second stake 134B is shown extending into a second passageway 124B defined by a second fluke 106B of staple 100. In some useful embodiments, an intermediate portion 180 of staple 100 extends tautly between first stake 134A and second stake 134B when the stakes are forming the bow-like shape shown in FIG. 14.

First fluke 106A of staple 100 defines a first passageway 124A. In FIG. 14, a distal portion 138 of first stake 134A of staple push rod 130 can be seen extending through first passageway 124A defined by first fluke 106A. A distal portion 138 of second stake 134B of staple push rod 130 can be seen extending through a second passageway 124B defined by second fluke 106B of staple 100.

In FIG. 14, a first shoulder 142A of first stake 134A is shown contacting proximal surface 108 of first fluke. Distal portion 138 of first stake 134A extends distally of first shoulder 142A and proximal portion 140 of first stake 134A extends proximally of first shoulder 142A. Proximal portion 140 of second stake 134B extends proximally of second shoulder 142B and distal portion 138 of second stake 134B extends distally of second shoulder 142B. In the embodiment of FIG. 14, proximal portion 140 of second stake 134B has a width larger than the width of distal portion 138 of second stake 134B so that the shoulder 142 of second stake 134B contacts proximal surface 108 of second fluke 106B to apply pushing forces thereto. Similarly, proximal portion 140 of first stake 134A has a width larger than the width of distal portion 138 of first stake 134A so that the shoulder 142 of first stake 134A contacts proximal surface 108 of first fluke 106A to apply pushing forces thereto.

Figure 15:
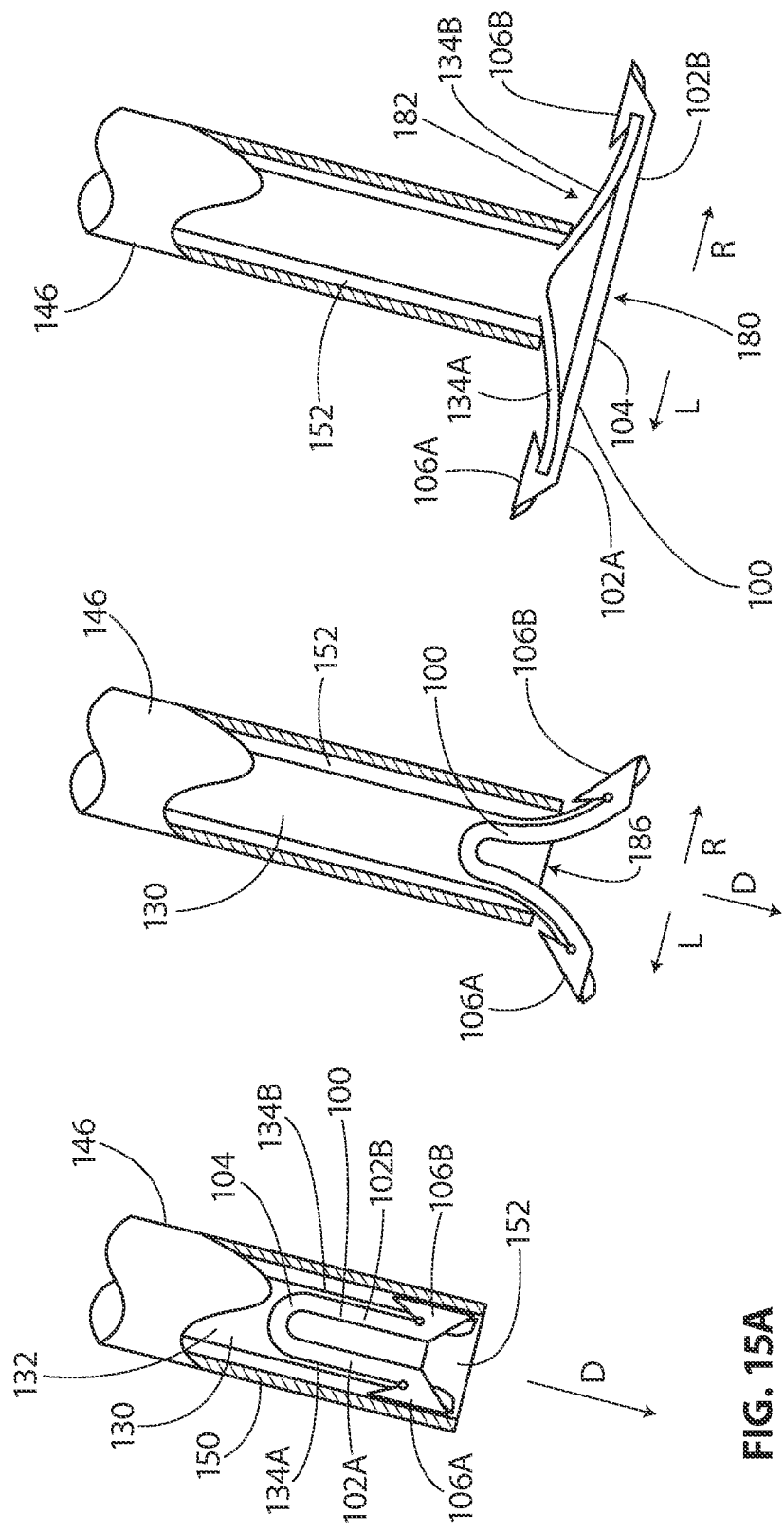
FIG. 15A through FIG. 15C are a series of stylized plan views illustrating an exemplary method in accordance with the present detailed description.

FIG. 15A through FIG. 15C are a series of stylized plan views illustrating an exemplary method in accordance with the present detailed description. FIG. 15A through FIG. 15C may be referred to collectively as FIG. 15. A distal direction is illustrated with an arrow D in FIG. 15. The exemplary method of FIG. 15 may be used, for example, to fix a sheet-like implant to a target tissue.

Each of these figures shows a fixation tool sheath 146 disposed about a distal portion of a staple push rod 130. Fixation tool sheath 146 comprises a wall 150 defining a lumen 152. Staple push rod 130 is slidingly disposed in lumen 152 in the embodiment of FIG. 15. For purposes of illustration, a portion of wall 150 is cut away in each figure, making the interior of lumen 152 visible. Staple push rod 130 of fixation tool 144 includes a shaft 132 and a pair of stakes 134 that are coupled to shaft 132. Stakes 134 include a first stake 134A and a second stake 134B. In FIG. 15, a distal portion of each stake 134 can be seen extending through a passageway defined by staple 100.

In FIG. 15A, staple 100 can be seen residing in a distal portion lumen 152. Staple 100 comprises a first arm 102A, a second arm 102B, and a bridge 104 extending from the proximal end of first arm 102A to the proximal end of second arm 102B. The distal end of first arm 102A abuts the proximal end of a first fluke 106A. Similarly, the distal end of second arm 102B abuts the proximal end of a second fluke 106B. In FIG. 15, first fluke 106A and second fluke 106B are shown extending distally from first arm 102A and second arm 102B, respectively.

FIG. 15B illustrates an exemplary configuration in which staple push rod 130 has been moved in a distal direction D relative to fixation tool sheath 146. With reference to FIG. 15B, it will be appreciated that staple 100 is now extending through a distal opening 186 defined by fixation tool sheath 146. Additionally, first fluke 106A of staple 100 has been moved in a first lateral direction L. Similarly, second fluke 106B of staple 100 has been moved in a second lateral direction R. With reference to FIG. 15B, it will be appreciated that first fluke 106A and second fluke 106B have moved laterally away from each other.

FIG. 15C illustrates an exemplary embodiment in which staple 100 is disposed outside of lumen 152 defined by fixation tool sheath 146. By comparing FIG. 15B and FIG. 15C, it will be appreciated that first fluke 106A of staple 100 has been moved further in the first lateral direction L and second fluke 106B has been moved further in the second lateral direction R. Additionally, it will be appreciated that first fluke 106A and second fluke 106B have moved laterally away from each other.

In FIG. 15C an intermediate portion 180 of staple 100 is shown extending along a generally straight path between first fluke 106A and second fluke 106B. In the exemplary embodiment of FIG. 15, intermediate portion 180 of staple 100 comprises first arm 102, second arm 102 and bridge 104. Some methods in accordance with the present detailed disclosure include the step of pulling the intermediate portion of a staple taut between a first fluke and a second fluke. With reference to FIG. 15, it will be appreciated that staple push rod 130 comprises a distal bow 182 formed of first stake 134A and second stake 134B. In FIG. 15, intermediate portion 180 of staple 100 is shown extending across distal bow 182 like a bowstring.

Figure 16:
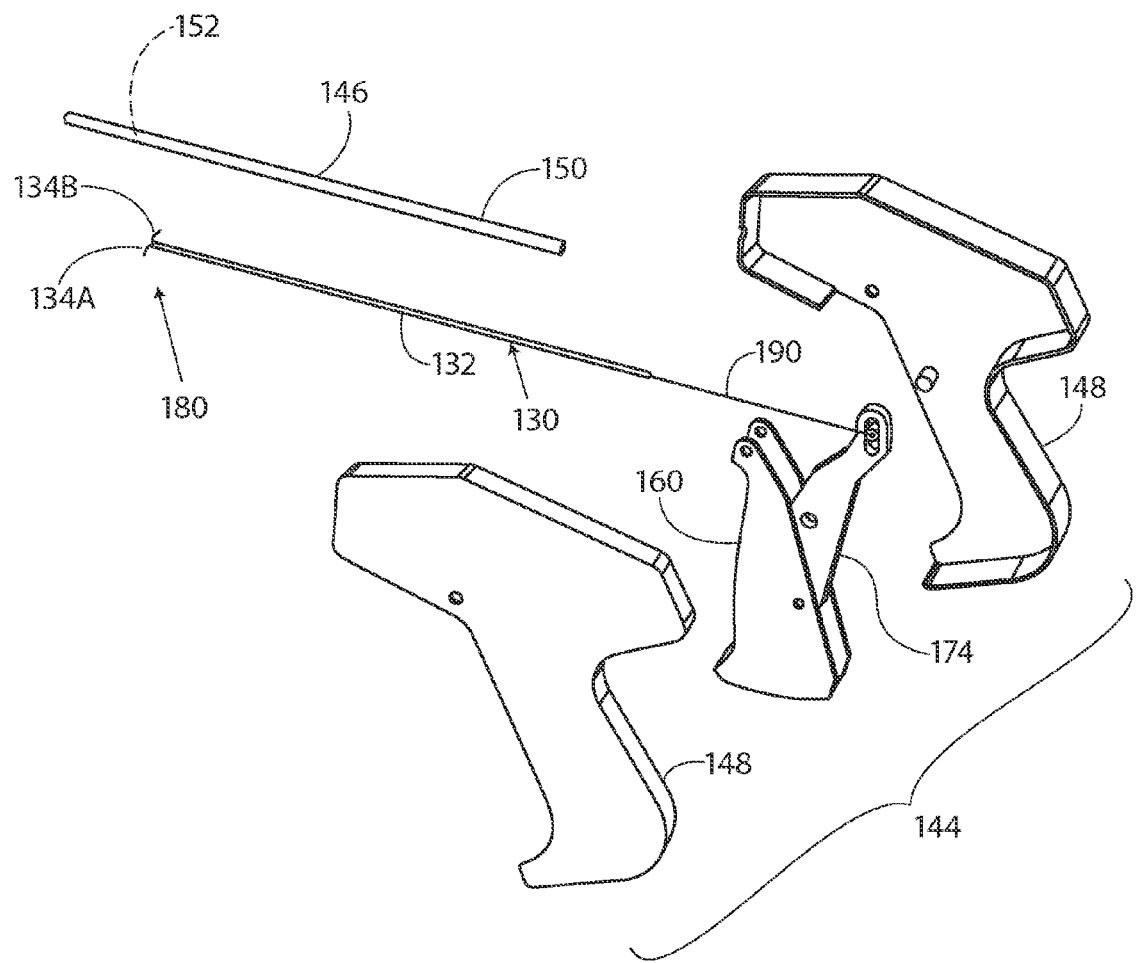
FIG. 16 is an exploded isometric view of an exemplary fixation tool in accordance with this detailed description.

FIG. 16 is an exploded isometric view of an exemplary fixation tool 144 in accordance with this detailed description. In the embodiment of FIG. 16, fixation tool 144 comprises a fixation tool sheath 146 and a handle 148. In FIG. 16, handle 148 is exploded into two pieces. A proximal portion of fixation tool sheath 146 is fixed to handle 148 when fixation tool 144 is in an assembled state. Fixation tool sheath 146 comprises a wall 150 defining a lumen 152. When fixation tool 144 is in an assembled state a staple push rod 130 extends into lumen 152 of fixation tool sheath 146. Staple push rod 130 comprises a bow 180 and a shaft 132. Bow 180 comprises a first stake 134A and a second stake 134B. Shaft 132 and a wire 190 are coupled between bow 180 and a lever 174. Lever 174 is coupled to a trigger 160. Trigger 160 is pivotably coupled to handle 148 of fixation tool 144 when fixation tool 144 is in an assembled state. In operation, staple push rod 130 will be advanced and/or retracted in an axial direction when trigger 160 is pivoted relative to handle 148.

Figure 17:
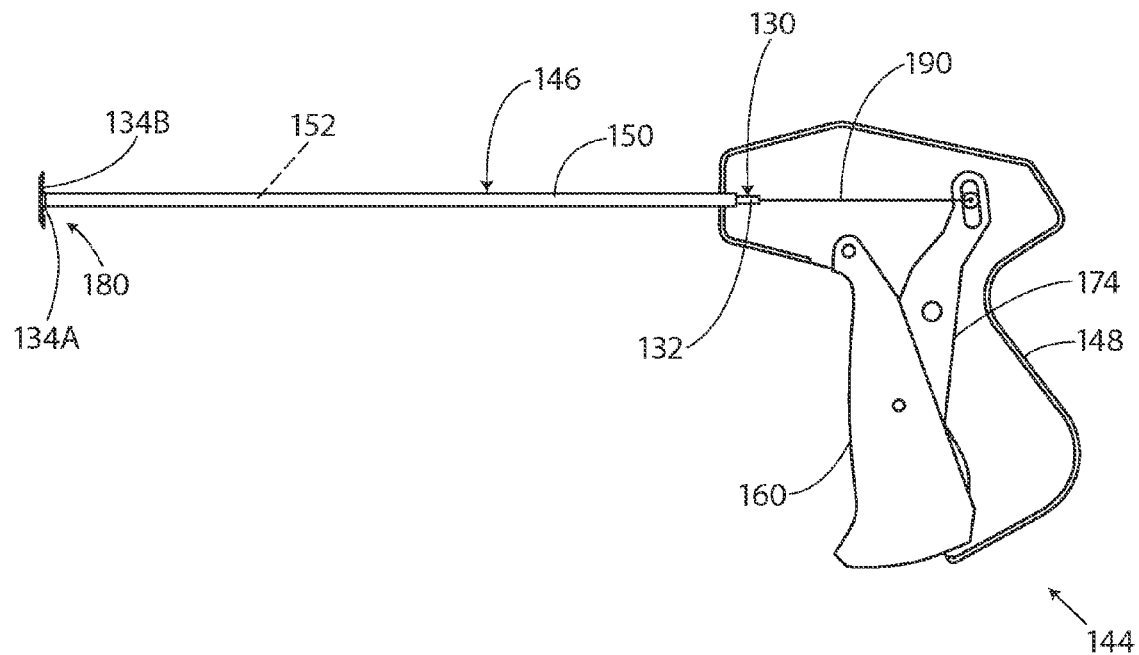
FIG. 17 is a side plan view of the fixation tool shown in FIG. 16.

FIG. 17 is a side plan view of fixation tool 144 shown in the previous figure. In FIG. 17, one piece of handle 148 is removed so that lever 174 can be seen residing in handle 148. Handle 148 of fixation tool 144 is fixed to a proximal portion of fixation tool sheath 146. Fixation tool sheath 146 comprises a wall 150 defining a lumen 152. A staple push rod 130 extends into lumen 152 of fixation tool sheath 146. Staple push rod 130 comprises a bow 180 and a shaft 132. Bow 180 comprises a first stake 134A and a second stake 134B. Shaft 132 and a wire 190 are coupled between bow 180 and a lever 174. Lever 174 is coupled to a trigger 160. Trigger 160 is pivotably coupled to handle 148 of fixation tool 144. In operation, staple push rod 130 will be advanced and/or retracted in an axial direction when trigger 160 is pivoted relative to handle 148.

Figure 18:
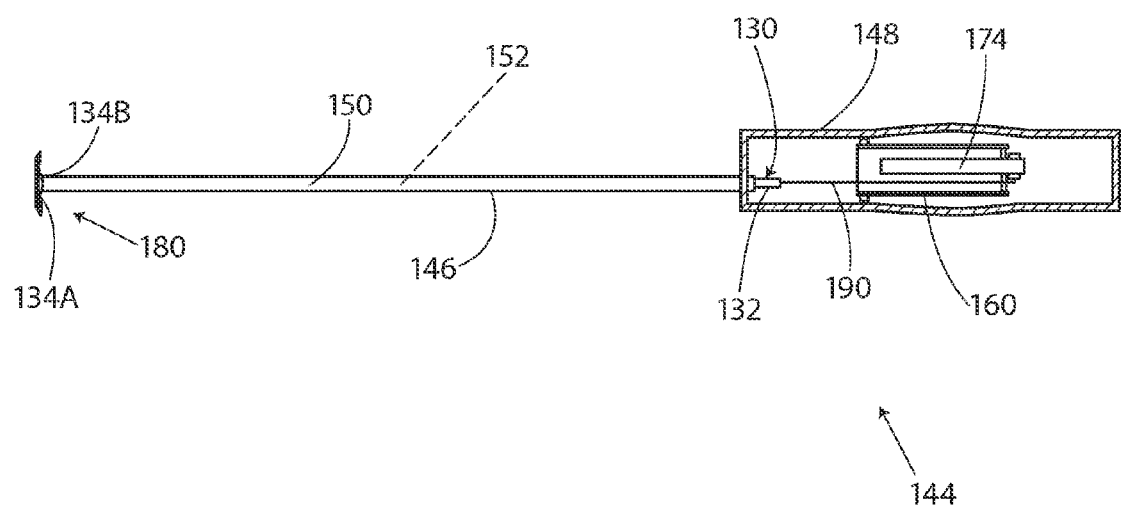
FIG. 18 is a top plan view of the fixation tool shown in FIGS. 17 and 18.

FIG. 18 is a top plan view of fixation tool 144 shown in the previous figure. Handle 148 of fixation tool 144 is shown in cross-section in FIG. 18 so that lever 174 can be seen residing in handle 148. Handle 148 of fixation tool 144 is fixed to a proximal portion of fixation tool sheath 146. Fixation tool sheath 146 comprises a wall 150 defining a lumen 152. A staple push rod 130 extends into lumen 152 of fixation tool sheath 146. Staple push rod 130 comprises a bow 180 and a shaft 132. Bow 180 comprises a first stake 134A and a second stake 134B. Shaft 132 and a wire 190 are coupled between bow 180 and lever 174. Lever 174 is coupled to a trigger 160. Trigger 160 is pivotably coupled to handle 148 of fixation tool 144. In operation, staple push rod 130 will be advanced and/or retracted in an axial direction when trigger 160 is pivoted relative to handle 148.

Figure 19:
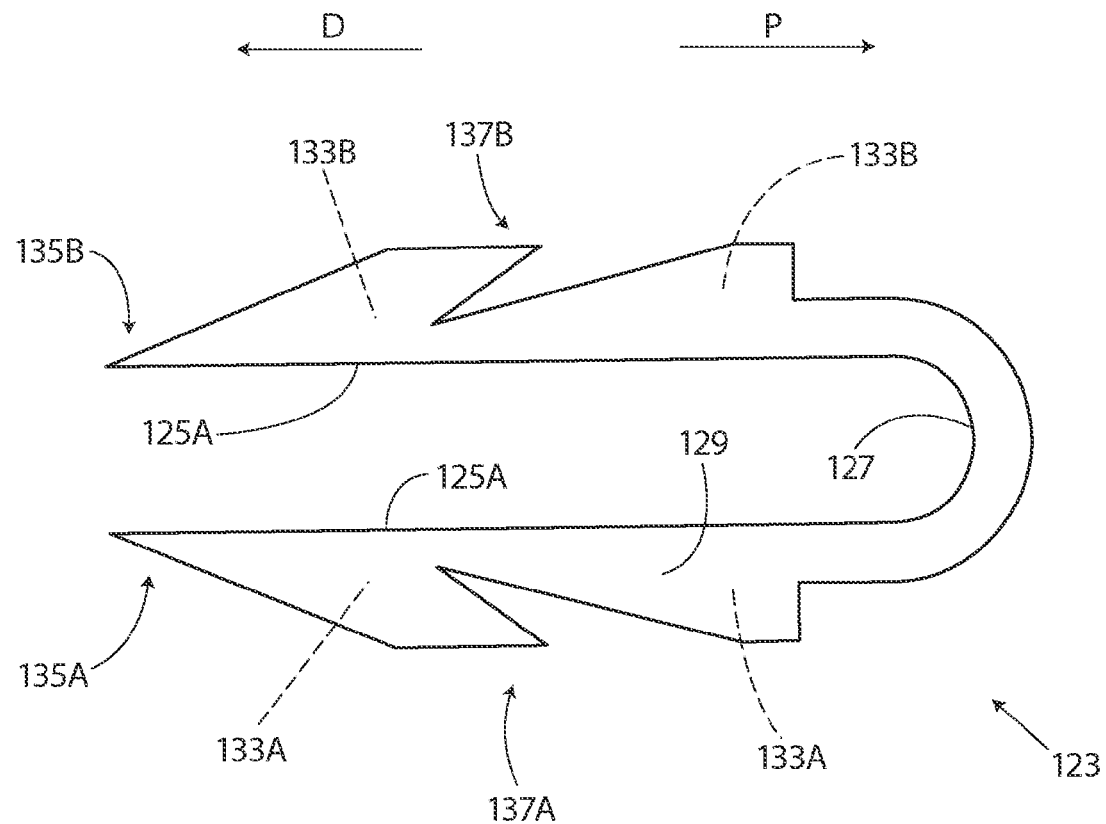
FIG. 19 is a plan view showing an additional exemplary embodiment of a staple in accordance with this detailed description.

FIG. 19 is a plan view showing an additional exemplary embodiment of a staple 123 in accordance with this detailed description. Staple 123 of FIG. 19 comprises a first arm 125A, a second arm 125B, and an intermediate portion 127 that extends between first arm 125A and second arm 125B. First arm 125A comprises a portion of a wall 129 defining a first lumen 133A. Second arm 125B comprises a portion of wall 129 defining a second lumen 133B.

With reference to FIG. 19, it will be appreciated that first arm 125A of staple 123 includes a first point 135A and a first barb 137A. Second arm 125B of staple 123 has a second point 135B and a second barb 137B. In the embodiment of FIG. 19, first point 135A and second point 135B are pointing in a distal direction D. Also in the embodiment of FIG. 19, first barb 137A and second barb 137B are pointing in a proximal direction P. Intermediate portion 127 of staple 123 is shown extending along an arcuate path between first arm 125A and second arm 125B in FIG. 19.

Figure 20:
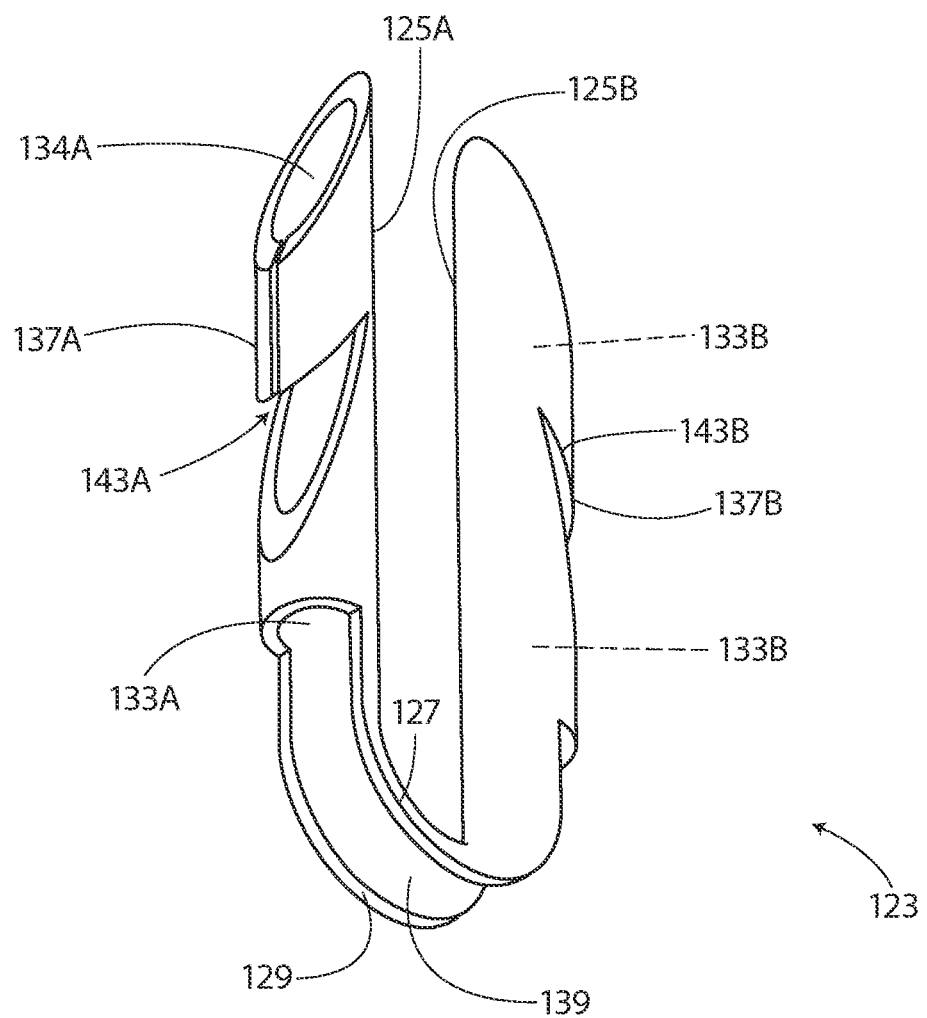
FIG. 20 is an isometric view further illustrating the staple shown in FIG. 19.

FIG. 20 is an isometric view showing staple 123 shown in the previous figure. In the embodiment of FIG. 20, staple 123 comprises a wall 129 defining a first lumen 133A, a second lumen 133B, and a channel 139. A first arm 125A of staple 123 is formed of the portion of wall 129 defining first lumen 133A. The portion of wall 129 defining second lumen 133B forms a second arm 125B. Channel 139 is defined by an intermediate portion 127 of staple 123.

In FIG. 20, intermediate portion 127 of staple 123 is shown extending along an arcuate path between first arm 125A and second arm 125B. First arm 125A defines a first notch 143A that fluidly communicates with first lumen 133A. With reference to FIG. 20, it will be appreciated that first notch 143A defines a first barb 137A of first arm 125A. Second arm 125B defines a second notch 143B that fluidly communicates with second lumen 133B. Second notch 143B defines a second barb 137B of second arm 125B in the embodiment of FIG. 20.

In some embodiments, staples such as staple 123 described above may have an internal lumen diameter of about 0.025 inches, and outside diameter of about 0.039 inches, and an overall length of about 0.450 inches. In some embodiments, staples may have a nominal diameter of less than about 0.039 inches. In some embodiments, staples may have a nominal diameter of between about 0.001 and 0.1 inches.

Figure 21A:
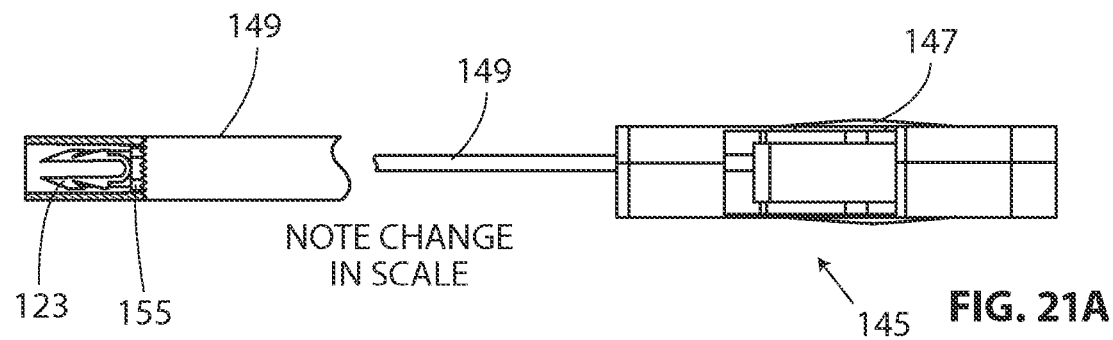
FIG. 21A and FIG. 21B illustrate multiple plan views of a fixation tool including a staple disposed in a sheath.
Figure 21B:
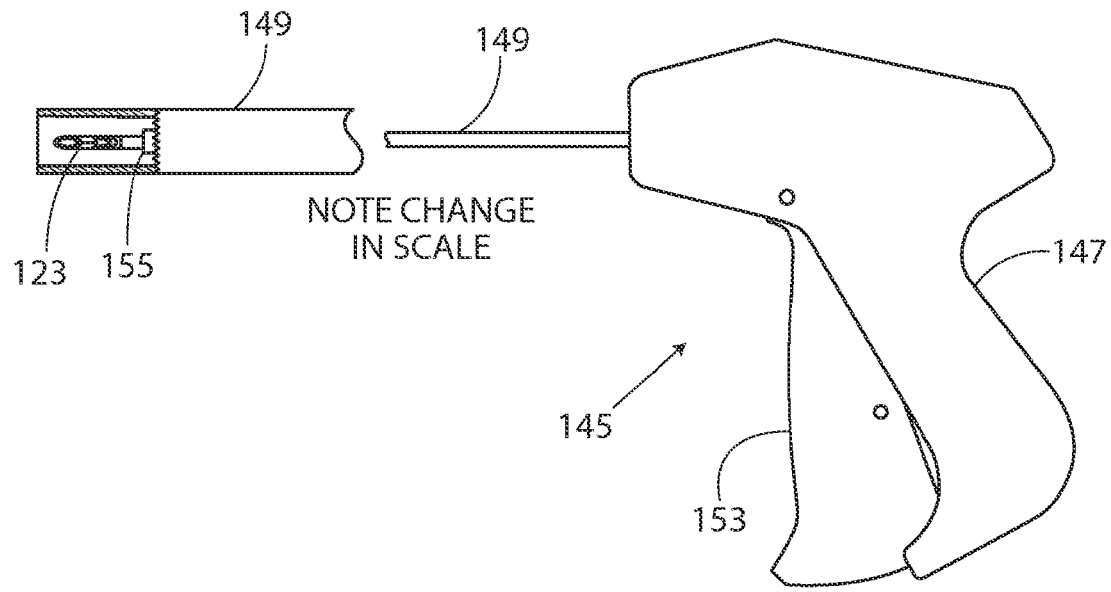

FIG. 21A and FIG. 21B illustrate multiple plan views of a fixation tool 145 including staple 123 shown in the previous figure. FIG. 21A and FIG. 21B may be referred to collectively as FIG. 21. It is customary to refer to multi-view projections using terms such as front view, top view, and side view. In accordance with this convention, FIG. 21A may be referred to as a top view of fixation tool 145 and FIG. 21B may be referred to as a side view of fixation tool 145. The terms top view and side view are used herein as a convenient method for differentiating between the views shown in FIG. 21. It will be appreciated that the elements shown in FIG. 21 may assume various orientations without deviating from the spirit and scope of this detailed description. Accordingly, the terms top view and side view should not be interpreted to limit the scope of the invention recited in the attached claims.

In the embodiment of FIG. 21, fixation tool 145 comprises a handle 147 and a fixation tool sheath 149 that is coupled to handle 147. In FIG. 21, staple 123 can be seen residing in a distal portion of fixation tool sheath 149. For purposes of illustration, the distal portion of fixation tool sheath 149 is enlarged in FIG. 21 to better show staple 123.

In the embodiment of FIG. 21, a trigger 153 is pivotably coupled to handle 147. Trigger 153 is operatively coupled to a staple pusher 155. In operation, staple pusher 155 is advanced and/or retracted when trigger 153 is pivoted relative to handle 147. With reference to FIG. 21, it will be appreciated that staple 123 is disposed on a distal portion of staple pusher 155. Accordingly, staple 123 can be moved distally and/or proximately by pivoting trigger 153 relative to handle 147 of fixation tool 145.

Figure 22A:
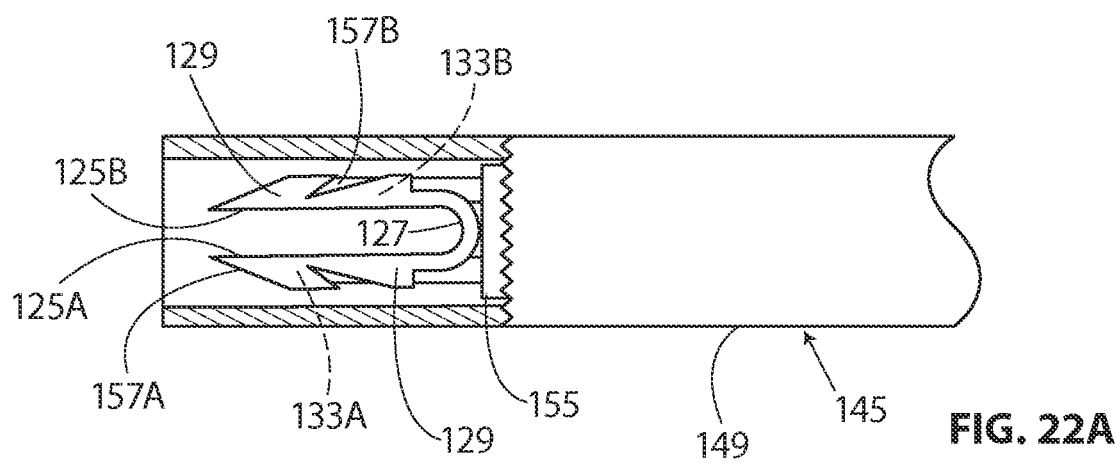
FIG. 22A is an enlarged top view further illustrating a distal portion of the fixation tool shown in FIG. 21.
Figure 22B:
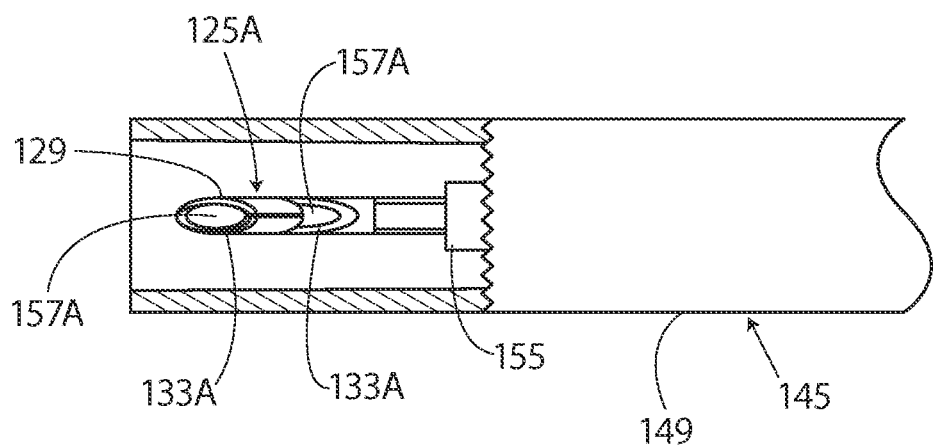
FIG. 22B is an enlarged side view further illustrating the distal portion of the fixation tool shown in FIG. 21.

FIG. 22A is a further enlarged top view of the distal portion of fixation tool 145 shown in the previous figure. FIG. 22B is an additional side view showing the distal portion of fixation tool 145. For purposes of illustration, a portion of fixation tool sheath 149 is cut-away in FIG. 22A and FIG. 22B. Accordingly, staple 123 can be seen residing in the distal portion of fixation tool sheath 149. FIG. 22A and FIG. 22B may be referred to collectively as FIG. 22.

With reference to FIG. 22, it will be appreciated that staple 123 comprises a first aim 125A, a second arm 125B, and an intermediate portion 127 that extends between first arm 125A and second aim 125B. First arm 125A comprises a portion of a wall 129 defining a first lumen 133A. Second arm 125B comprises a portion of wall 129 defining a second lumen 133B. Staple 123 is disposed on a staple pusher 155 of fixation tool 145 that extends into fixation tool sheath 149. In the exemplary embodiment of FIG. 22, staple pusher 155 comprises a first strut 157A and a second strut 157B. In FIG. 22, first strut 157A can be seen extending into first lumen 133A defined by first arm 125A. Second strut 157B extends into second lumen 133B defined by second arm 125B.

Figure 23:
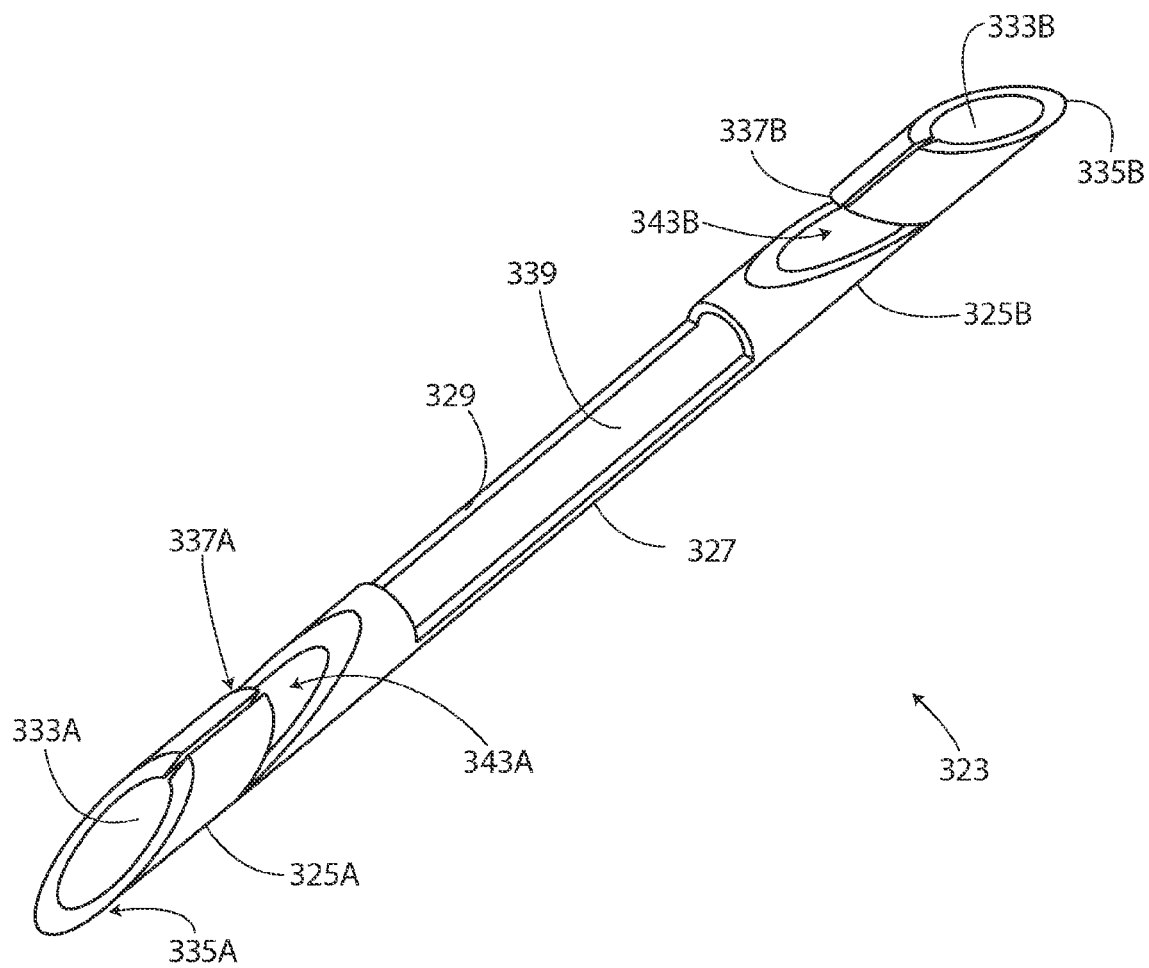
FIG. 23 is an isometric view showing an additional exemplary staple in accordance with the present detailed description.

FIG. 23 is an isometric view showing an additional exemplary staple 323 in accordance with the present detailed description. Staple 323 of FIG. 23 comprises a first arm 325A, a second arm 325B, and an intermediate portion 327 that extends between first arm 325A and second arm 325B. First arm 325A comprises a portion of a wall 329 defining a first lumen 333A. With reference to FIG. 23, it will be appreciated that first arm 325A includes a first point 335A and a first barb 337A. In the embodiment of FIG. 23, first barb 337A is defined by a first notch 343A.

Second arm 325B comprises a portion of wall 329 defining a second lumen 333B. Second arm 325B defines a second notch 343B that fluidly communicates with second lumen 333B. With reference to FIG. 23, it will be appreciated that second notch 343B defines second barb 337B of second arm 325B. A second point 335B of second arm 325B is also visible in FIG. 23. In FIG. 23, intermediate portion 327 of staple 323 is shown extending between first arm 325A and second arm 325B. Intermediate portion 327 of staple 323 defines a channel 339 that fluidly communicates with first lumen 333A and second lumen 333B.

While exemplary embodiments of the present invention have been shown and described, modifications may be made, and it is therefore intended in the appended claims and subsequently filed claims to cover all such changes and modifications which fall within the true spirit and scope of the invention.

What is claimed is:

1. A device for attaching a sheet-like implant to a target tissue, comprising:
a sheath having a distal end configured to be pressed against the target tissue; and
a staple push rod disposed within at least a portion of the sheath and slidable relative thereto, the staple push rod including a pair of stakes, each stake dimensioned to abut a surface of a staple to apply pushing forces thereto;
wherein the staples and stakes are flexed to assume a bow-like shape such that an intermediate portion of the staple extends tautly in tension between the first stake and the second stake when the stakes are extending beyond the distal end of the sheath.

2. The device of claim 1, wherein each stake has a distal portion and a proximal portion, each distal portion being dimensioned to extend into a passage defined by the staple, each proximal portion having a width larger than a width of each distal portion so that a shoulder of each proximal portion contacts a proximal surface of the staple to apply pushing forces thereto.

3. The device of claim 1, wherein the stakes are biased to expand against an inner surface of the sheath.

4. The device of claim 1, wherein the intermediate portion of the staple includes a first arm, a second arm, and a bridge.

5. The device of claim 1, wherein the first stake and the second stake extend away from each other when the stakes are assuming the bow-like shape.

6. The device of claim 1, wherein the sheath having a proximal end, a distal end and a lumen extending therebetween, at least a portion of the staple push rod extending into the lumen and slidable relative thereto.

7. The device of claim 6, wherein the first stake and the second stake are disposed in the lumen of the sheath.

8. The device of claim 6, wherein:
the sheath defines a distal opening fluidly communicating with the lumen; and
the staple push rod is slidably disposed in the lumen so as to urge relative movement between the stakes and the sheath such that the stakes can be advanced through the distal opening defined by the sheath so that the stakes are free to assume the bow-like shape.

9. The device of claim 6, wherein:
the stakes have a first lateral extent when the stakes are free to assume the bow-like shape; and
the lumen of the sheath has a lumen dimension smaller than the first lateral extent such that the sheath holds the stakes in a compact configuration.

10. The device of claim 6, wherein:
the stakes have a first lateral extent when the stakes are free to assume the bow-like shape; and
the lumen of the sheath has a lumen dimension smaller than the first lateral extent; and
the stakes are sufficiently flexible to allow the stakes to be advanced into the lumen of the sheath.

11. The device of claim 1, wherein a distal-most portion of each stake extends across a leading edge of each fluke of the staple.

12. The device of claim 1, the staple including a first arm and a second arm, wherein the first stake and second stake are configured to pull the first arm of the staple and second arm of the staple such that an end of the first arm and an end of the second arm extend away from each other when the first and second stakes extend beyond the distal end of the sheath.

13. The device of claim 1, the staple including a first arm and a second arm, wherein the first arm and second arm define a longitudinal staple axis when the first arm and second arm extend tautly between the first stake and second stake, wherein the longitudinal staple axis is substantially perpendicular to a longitudinal axis of the sheath.

14. The device of claim 1, wherein the device is configured to deploy the staple in the target tissue such that an end of the first arm of the staple and an end of the second arm of the staple extend away from each other.

15. A device for attaching a sheet-like implant to a target tissue, comprising:
a sheath having a distal end configured to be pressed against the target tissue; and
a staple push rod disposed within at least a portion of the sheath and slidable relative thereto, the staple push rod including a first stake and second stake, each stake dimensioned to abut a surface of a staple to apply pushing forces thereto, the staple including a first arm with a lumen, a second arm with a lumen, and a bridge extending between the first arm and second arm, the first stake configured to pass through and engage with the lumen of the first arm and the second stake configured to pass through and engage with the lumen of the second arm;

wherein the staples and stakes are flexed to assume a bow-like shape such that a portion of the staple extends tautly between the first stake and the second stake when the stakes are extending beyond the distal end of the sheath.

16. The device of claim 15, wherein the first stake and second stake are configured to pull the first arm of the staple and second arm of the staple such that an end of the first arm and an end of the second arm extend away from each other when the first and second stakes extend beyond the distal end of the sheath.

17. The device of claim 16, wherein the first arm and second arm define a longitudinal staple axis when the first arm and second arm extend tautly between the first stake and second stake, wherein the longitudinal staple axis is substantially perpendicular to a longitudinal axis of the sheath.

18. The device of claim 15, wherein the portion of the staple extends in tension between the first stake and second stake.

19. The device of claim 15, wherein the first stake and the second stake extend away from each other when the stakes are assuming the bow-like shape.

20. The device of claim 15, wherein the device is configured to deploy the staple in the target tissue such that an end of the first arm of the staple and an end of the second arm of the staple extend away from each other.

* * * * *